US008236547B2

(12) United States Patent
Mikkelsen et al.

(10) Patent No.: US 8,236,547 B2
(45) Date of Patent: Aug. 7, 2012

(54) INCREASED ETHANOL PRODUCTION IN RECOMBINANT BACTERIA

(75) Inventors: Marie Just Mikkelsen, Bronshoj (DK); Shuo Yao, Soborg (DK)

(73) Assignee: Biogasol IPR APS, Ballerup (DK)

( * ) Notice: Subject to any disclaimer, the term of this patent is extended or adjusted under 35 U.S.C. 154(b) by 0 days.

(21) Appl. No.: 13/055,079

(22) PCT Filed: Jul. 22, 2009

(86) PCT No.: PCT/EP2009/059421
§ 371 (c)(1),
(2), (4) Date: Mar. 31, 2011

(87) PCT Pub. No.: WO2010/010116
PCT Pub. Date: Jan. 28, 2010

(65) Prior Publication Data
US 2011/0287501 A1    Nov. 24, 2011

Related U.S. Application Data

(60) Provisional application No. 61/100,504, filed on Sep. 26, 2008.

(30) Foreign Application Priority Data

Jul. 24, 2008   (EP) .................................... 08161066

(51) Int. Cl.
*C12N 1/20* (2006.01)
*C12P 7/06* (2006.01)
(52) U.S. Cl. .................................... 435/252.3; 435/161
(58) Field of Classification Search ............... 435/252.3, 435/161
See application file for complete search history.

(56) References Cited

FOREIGN PATENT DOCUMENTS

| JP | 2003-516721 A | 5/2003 |
|----|---------------|--------|
| WO | 01/21825 A2 | 3/2001 |
| WO | 2006117536 A1 | 9/2006 |
| WO | 2007053600 A2 | 5/2007 |
| WO | 2007115228 A2 | 10/2007 |
| WO | 2007134607 A1 | 11/2007 |
| WO | 2008006037 A2 | 1/2008 |

OTHER PUBLICATIONS

Berrios-Rivera et al., "The Effect of NAPRTase Overexpression on the Total Levels of NAD, The NADH/NAD+ Ratio, and the Distribution of Metabolites in *Escherichia coli*", Metabolic Engineering, Academic Press, US, vol. 4, pp. 238-247, 2002.
Vasconcelos et al., "Regulation of Carbon and Electron Flow in *Clostridium acetobutylicum* Grown in Chemostat Culture at Neutral pH on Mixtures of Glucose and Glycerol", Journal of Bacteriology, vol. 176, No. 3, pp. 1443-1450, 1994.
Berrios-Rivera et al., "The effect of carbon sources and lactate dehydrogenase deletion on 1,2-propanediol production in *Escherichia coli*", J. Ind Microbiol Biotechnol, vol. 30, pp. 34-40, 2003.
Gonzalez-Pajuelo et al., "Microbial Conversion of Glycerol to 1,3-Propanediol: Physiological Comparison of a Natural Producer, *Clostridium butyricum* VPI 3266, and an Engineered Strain, *Clostridium acetobutylicum* DG1(pSPD5)", Applied and Environment Microbiology, vol. 72, No. 1, pp. 96-101, 2006.
Hoseki et al., "Directed Evolution of Thermostable Kanamycin-Resistance Gene: A Convenient Selection Marker for *Thermus thermophilus*", J. BioChem, vol. 126, pp. 951-956, 1999.
Larsen et al., "*Thermoanaerobacter mathranii* sp. nov., an ethanol-producing, extremely thermophilic anaerobic bacterium from a hot spring in Iceland", Arch Microbiol, vol. 168, pp. 114-119, 1997.
Hungate, R. E., "A Roll Tube Method for Cultivation of Strict Anaerobes", Chapter IV, pp. 117-132, 1969.
Bryant, M. P., "Commentary on the Hungate technique for culture of anaerobic bacteria1", The American Journal of Clinical Nutrition, vol. 25, pp. 1324-1328, 1972.
Bjerre et al., "Pretreatment of Wheat Straw Using Combined Wet Oxidation and Alkaline Hydrolysis Resulting in Convertible Cellulose and Hemicellulose", Biotechnology and Bioengineering, vol. 49, pp. 568-577, 1996.
Burton, R. M. (Colowick et al.), "Methods in Enzymology", vol. 1, pp. 397-401, 1955.
Bradford, M. M., "A Rapid and Sensitive Method for the Quantitation of Microgram Quantities of Protein Utilizing the Principle of Protein-dye Binding", Analytical Biochemistry, vol. 72, pp. 248-254, 1976.
Desai et al., "Cloning of L-lactate dehydrogenase and elimination of lactic acid production via gene knockout in *Thermoanaerobacterium saccharolyticum* JW/SL-YS485", Appl. Microbiol Biotechnol, vol. 65, pp. 600-605, 2004.
Lynd et al., "Salt Accumulation Resulting from Base Added for pH Control, and Not Ethanol, Limits Growth of *Thermoanaerobacterium thermosaccharolyticum* HG-8 at Elevated Feed Xylose Concentrations in Continuous Culture", Biotechnol Prog, vol. 17, pp. 118-125, 2001.
Yazdani et al., "Engineering *Eschrichia coli* for the efficient conversion of glycerol to ethanol and co-products, 30th Annual Symposium on Biotechnology for Fuels and Chemicals", pp. No. 40 and 54, May 2008.
Brinen et al., "Crystal Structure of a Zinc-containing Glycerol Dehydrogenase (TM0423) from *Thermotoga maritima* at 1.5 ANG Resolution", Proteins, vol. 50, No. 2, pp. 371-374, 2003.
Yazdani, S. S. et al., "Engineering *Eschrichia coli* for the efficient conversion of glycerol to ethanol and co-products," Metabolic Engineering, Academic Press, US, vol. 10, No. 6, pp. 340-351, 2008.
International Search Report in corresponding PCT/EP2009/059421 dated Oct. 9, 2009.
International Preliminary Report on Patentability in corresponding PCT/EP2009/059421 dated Oct. 4, 2010.
Ruzheinikov, S.N. et al. "Glycerol Dehydrogenase: Structure, Specificity, and Mechanism of a Family III Polyol Dehydrogenase", Structure, vol. 9, pp. 789-802, Sep. 2001.

*Primary Examiner* — Tekchand Saidha
(74) *Attorney, Agent, or Firm* — Roberts Mlotkowski Safran & Cole P.C.

(57) ABSTRACT

The invention pertains to a recombinant bacterium with enhanced ethanol production characteristics when cultivated in a growth medium comprising glycerol. The recombinant bacterium comprises an inserted heterologous gene encoding glycerol dehydrogenase, and/or an up-regulated native gene encoding glycerol dehydrogenase. Particularly there is provided the recombinant bacterium BG1G1 of the *Thermoanaerobacter mathranii* species with an inserted heterologous gene encoding the E.C. 1.1.1.6 type, a NAD dependent glycerol dehydrogenase obtained from *Thermotoga maritima*.

16 Claims, 8 Drawing Sheets

INCREASED ETHANOL PRODUCTION IN RECOMBINANT BACTERIA

CROSS-REFERENCE TO RELATED APPLICATIONS

The present application is a U.S. national phase of PCT/EP2009/059421 filed on Jul. 22, 2009 ("PCT application"), which claims priority from European Application No. 08161066.9 filed on Jul. 24, 2008 and U.S. Provisional Application No. 61/100,504 filed on Sep. 26, 2008, both of which are hereby incorporated by reference in their entirety into the present application. The PCT application, incorporated by reference herein, includes any amendments entered in the PCT application.

TECHNICAL FIELD

The present invention relates to recombinant bacteria with increased ethanol production capabilities when cultivated in media comprising glycerol. The recombinant bacteria comprise an inserted heterologous gene encoding glycerol dehydrogenase, and/or an up-regulated native gene encoding glycerol dehydrogenase.

BACKGROUND OF THE INVENTION

World ethanol production totalled 46 billion litres in 2005 and is rapidly increasing (EU commission, 2006). The production of ethanol can be either from starch or sugar, which primarily consist of glucose or from lignocellulosic material such as wood, straw, grass, or agricultural and household waste products. The main constituents of lignocellulosic material are the polymers cellulose and hemicellulose. While cellulose is a rather homogenous polymer of glucose, the hemicellulose is a much more complex structure of different pentoses and hexoses. The complex composition of hemicellulose requires different means of pre-treatment of the biomass to release the sugars and also different fermenting organisms. To produce ethanol by fermentation a microorganism able to convert sugars into ethanol rapidly and with very high ethanol yields is required. Traditionally, organisms such as the yeast *Saccharomyces cerevisiae* or the bacterium *Zymomonas mobilis* have been used, but these organisms have limitations especially when it comes to fermentation of the pentose sugars from hemicellulose and the risk of contamination.

Lignocellulosic material is the most abundant source of carbohydrate on earth, and the second most important sugar in this biomass is xylose—a pentose sugar. If production of ethanol from lignocellulosic biomass is to be economically favourable, then all sugars must be used, including pentoses.

Thermophilic anaerobic bacteria have proven to be promising candidates for production of ethanol from lignocellulosic materials (WO 2007/134607). The primary advantages are their broad substrate specificities and high natural production of ethanol. Moreover, ethanol fermentation at high temperatures (55-70° C.) has many advantages over mesophilic fermentation. One important advantage is the minimization of the problem of contamination in continuous cultures, since only few microorganisms are able to grow at such high temperatures.

WO 2007/053600A describes how close to stoichiometric yields of ethanol from glucose and xylose can be obtained by deleting the genes coding for lactate dehydrogenase, phosphotransacetylase and acetate kinase in *Thermoanaerobacterium saccharolyticum*. However, this approach may not be applicable in thermophilic organisms having multiple phosphotransacetylase and acetate kinase genes and does not facilitate utilization of glycerol.

Ethanol yield is of great importance for the production economy of bioethanol, since increased income can be obtained without an increase in biomass price or production costs. For *Escherichia coli* it has been shown that once the enzyme levels and substrate are no longer limiting, cofactor availability and the ratio of the reduced to oxidized form of the cofactor can become limiting for alcohol yield (Berrios-Rivera et al., 2002).

It has been shown that addition of glycerol to the growth medium of certain Clostridia can increase the production of alcohols (Vasconcelos et al., 1994). However, optimal alcohol production was achieved at a glycerol/glucose ratio of 2, and glycerol is therefore considered to be a major expense.

A glycerol dehydrogenase gene has been introduced into *Escherichia coli* to promote the production of 1,2-propanediol (Berrios-Rivera et al., 2003) and into *Clostridium acetobutylicum* to promote production of 1,3-propanediol (Gonzalez-Pajuelo et al., 2006). In both cases the glycerol dehydrogenase is in the direct pathway to the produced propanediol, and no production of propanediol occurs without the presence of the gene. The major function of the glycerol dehydrogenase is not to change the redox balance of the cell, but rather to provide a new pathway.

It is therefore one object of the present invention to provide recombinant bacteria, in particular thermophilic anaerobic bacteria, with increased ethanol production capabilities which are capable of overcoming the above mentioned obstacles.

SUMMARY OF THE INVENTION

Accordingly, the present invention pertains to a recombinant bacterium having enhanced ethanol production characteristics when cultivated in a growth medium comprising glycerol. The recombinant bacterium comprises an inserted heterologous gene encoding glycerol dehydrogenase, and/or an up-regulated native gene encoding glycerol dehydrogenase.

The invention further relates to a method for producing ethanol, by culturing a bacterium according to the invention said method comprising the steps of culturing a bacterium according to the invention in a growth medium comprising glycerol and a polysaccharide source under suitable conditions.

Finally, there is provided a method for producing a recombinant bacterium having enhanced ethanol production characteristics when cultivated in a growth medium comprising glycerol, wherein the method comprises transforming a parental bacterium by the insertion of a heterologous gene encoding glycerol dehydrogenase, and/or up-regulating a native gene encoding glycerol dehydrogenase; and obtaining the recombinant bacterium.

DETAILED DESCRIPTION OF THE INVENTION

Figure 1:
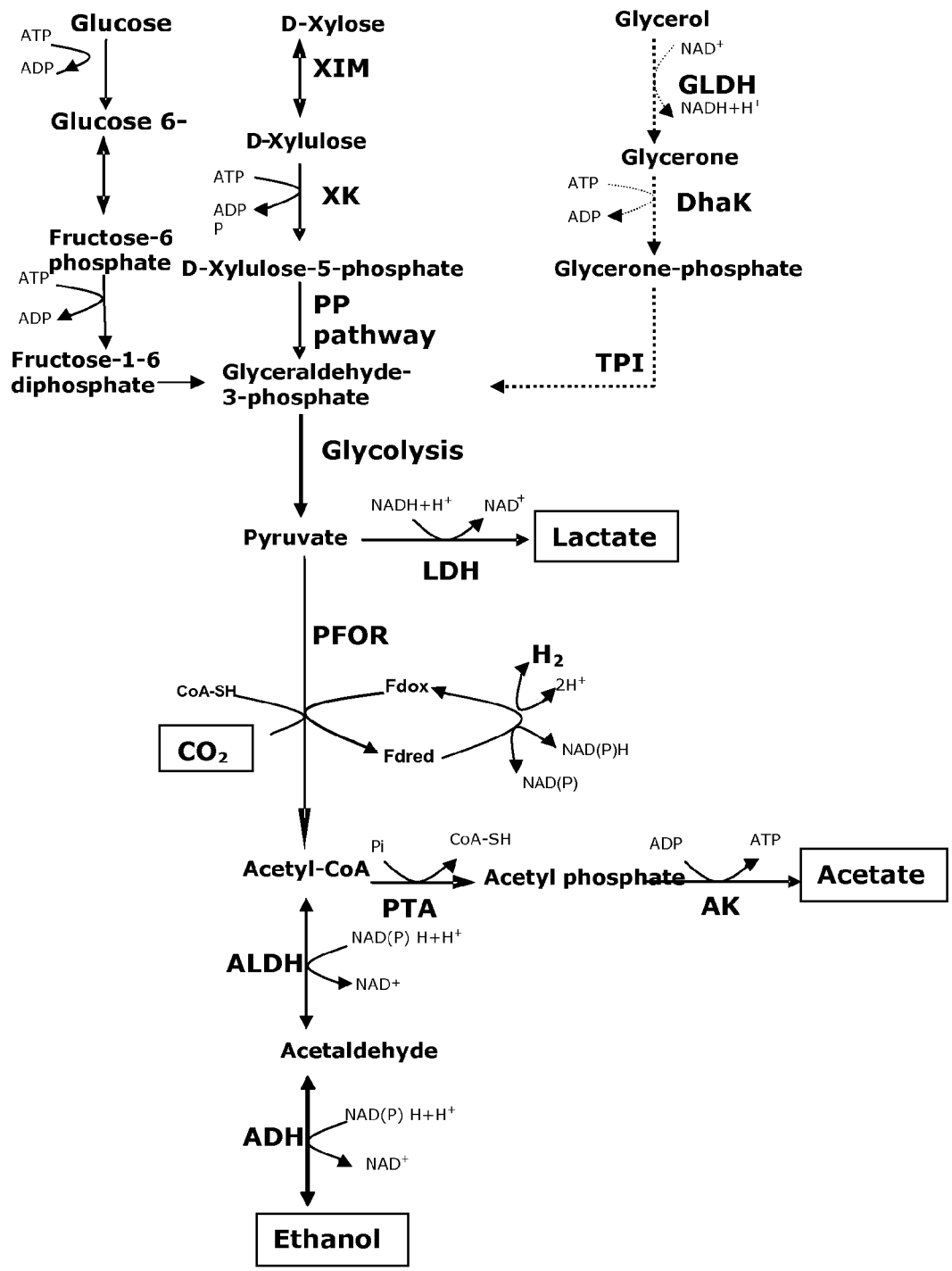
FIG. 1. Model of anaerobic metabolism in thermophilic anaerobic ethanol producing bacteria and diagram illustrating the native cofactor independent upper part of glycolysis pathway and the newly introduced NAD+ dependent glycerol degradation pathway. —Original $NAD^+$ independent pathway, ---- Newly added $NAD^+$ dependent pathway, XIM=Xylose isomerase, XK=Xylose kinase, PP pathway=pentose phosphate pathway, GLDH=Glycerol dehydrogenase, DhaK=Dihydroxyacetone kinase, TPI=Triosephosphate isomerase. LDH=Lactate dehydrogenase, PFOR=Pyruvate-ferredoxin oxidoreductase, PTA=Phosphotransacetylase, AK=Acetate kinase, ALDH=Acetaldehyde dehydrogenase, PDC=Pyruvate decarboxylase, ADH=Alcohol dehydrogenase.

The present invention pertains to recombinant bacteria with enhanced ethanol production characteristics. More specifically it has been found that ethanol production characteristics for bacteria, when cultivated in growth media comprising glycerol, can be significantly enhanced by the insertion of a heterologous gene coding for glycerol dehydrogenase and/or by up-regulation of an already existing native gene encoding glycerol dehydrogenase.

In the present context the term "ethanol" is to be understood as a straight-chain alcohol with the molecular formula $C_2H_5OH$. Ethanol is also commonly referred to as "ethyl alcohol", "grain alcohol" and "drinking alcohol". An often used alternative notation for ethanol is $CH_3$—$CH_2$—OH, which indicates that the carbon of a methyl group ($CH_3$—) is attached to the carbon of a methylene group (—$CH_2$—), which is attached to the oxygen of a hydroxyl group (—OH). A widely used acronym for ethanol is EtOH.

Glycerol is a chemical compound that is available on the world market at a reasonable cost. In the present context the term "glycerol" is intended to mean a chemical compound with the general formula HOCH2CH(OH)CH2OH. Glycerol is a colourless, odourless, viscous liquid and is widely used in pharmaceutical formulations. Glycerol is also commonly called glycerin or glycerine, it is a sugar alcohol, and is sweet-tasting and of low toxicity. Glycerol is a 10% by-product of biodiesel production and the price of glycerol has dramatically decreased during the last few years due to the increasing production of biodiesel. As the production of biodiesel is increasing exponentially, the glycerol generated from the transesterification of plant oils is also generated in increasing amounts. Another source of glycerol is the yeast based ethanol fermentations. Thus, the increasing production of starch based ethanol will also lead to increasing availability of glycerol.

The bacteria according to invention comprises, as described above, an inserted heterologous gene and/or an up-regulated native gene encoding a glycerol dehydrogenase. A number of useful enzymes having glycerol dehydrogenase activity are known in the art. In presently preferred embodiments the glycerol dehydrogenase is selected from glycerol dehydrogenase (E.C 1.1.1.6); Glycerol dehydrogenase (NADP(+)) (E.C. 1.1.1.72); Glycerol 2-dehydrogenase (NADP(+)) (E.C. 1.1.1.156); and Glycerol dehydrogenase (acceptor) (E.C. 1.1.99.22).

Useful genes encoding the above mentioned glycerol dehydrogenases may be derived from a number of different sources such as microorganisms, including fungi and bacteria, and animal cells, such as mammalian cells and insect cells.

In a presently preferred embodiment the glycerol dehydrogenase is, as mentioned above, of the E.C. 1.1.1.6 type, i.e. a NAD dependent glycerol dehydrogenase (alternative name "NAD-linked glycerol dehydrogenase") which catalyses the reaction: Glycerol+NAD(+)<=>glycerone+NADH. Genes encoding the E.C. 1.1.1.6 type, i.e. a NAD dependent glycerol dehydrogenase may be obtained from a bacterium of the *Thermotoga* group of bacteria such as *Thermotoga maritima*.

In other embodiments the glycerol dehydrogenase gene is derived from a bacterium belonging to the *Geobacillus* group of bacteria, such as *Geobacillus stearothermophilus*. It is also contemplated that useful glycerol dehydrogenase genes may be derived from other bacteria such as *Escherichia coli, Salmonella typhimurium, Clostridium botulinum, Vibrio vulnificus, Clorobium ferrooxidans, Geobacter Lovleyi, Ruminococcus gnavus, Bacillus coagulans, Klebsiella pneumoniae, Citrobacter koseri, Shigella boydii, Klebsiella pneumoniae, Clostridium butyricum, Vibrio* sp., and *Serratia proteamaculans*. Useful genes encoding a number of E.C. 1.1.1.6 type glycerol dehydrogenases are shown in the accompanying sequence listing (SEQ ID NOs 1-17).

Accordingly, the heterologous gene encoding an E.C. 1.1.1.6 type glycerol dehydrogenase may in useful embodiments be selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17.

Methods for the preparation and the incorporation of these genes into microorganisms are well known in the art, for example from Sambrook & Russell "Molecular Cloning: A Laboratory Manual" (Third Edition), Cold Spring Harbor Laboratory Press which i.a. describes how genes may be inserted, deleted or substantially inactivated using suitable gene manipulation tools and genetic engineering procedures.

Chromosomal integration of foreign genes may offer several advantages over plasmid-based constructions. Accordingly, the heterologous glycerol dehydrogenase gene may in accordance with the invention be incorporated into the chromosome of the bacterium. In certain embodiments, the heterologous glycerol dehydrogenase gene is inserted into a lactate dehydrogenase encoding region of said bacterium. In further embodiments the heterologous gene encoding a glycerol dehydrogenase is inserted into a phosphotransacetylase encoding region of the bacterium according to the invention.

In yet further embodiments, the heterologous glycerol dehydrogenase gene is inserted into an acetate kinase encoding region of said bacterium.

The heterologous gene encoding glycerol dehydrogenase may be operably linked to an inducible, a regulated or a constitutive promoter. In useful embodiments the promoter is a xylose inducible promoter.

Up-regulation of gen-expression is a process which occurs within a cell triggered by a signal (originating internal or external to the cell) which results in increased expression of one or more genes and as a result the protein(s) encoded by those genes. Thus, it is also within the scope of the invention that the recombinant bacterium may be obtained by transforming a parental bacterium by up-regulating an already present native gene in the parental bacterium which encodes a glycerol dehydrogenase. A number of methods and systems for up-regulation of genes are well known in the art, i.a. inducible systems in which the system is off unless there is the presence of an inducer molecule that allows for gene expression. A well known system is the Lac operon which consists of three adjacent structural genes, a promoter, a terminator, and an operator. The lac operon is regulated by several factors including the availability of glucose and of lactose.

In a specific embodiment, the heterologous gene encoding glycerol dehydrogenase, and/or the up-regulated native gene encoding glycerol dehydrogenase over-expressed on a multicopy plasmid.

The bacteria selected for modification are said to be "wild-type", i.e. they are not laboratory-produced mutants (also referred to in the present context as "parental bacteria" and "parental non-recombinant bacteria"). The wild-type bacteria may be isolated from environmental samples expected to contain useful ethanol producing bacterial species. Isolated wild-type bacteria will have the ability to produce ethanol but, unmodified, with a relatively low yield. The isolates may in useful embodiments be selected for their ability to grow on hexose and/or pentose sugars, and oligomers thereof, at thermophilic temperatures.

The selected wild-type bacteria and the resulting recombinant bacteria of the invention, may be cultured under conventional culture conditions, depending on the bacteria chosen. The choice of substrates, temperature, pH and other growth conditions can be selected based on known culture requirements.

However, as will be seen from the following examples, the present invention is particular well-suited for improving ethanol yields in thermophilic recombinant bacteria. Thus, the recombinant bacterial strains according to the invention are preferably thermophilic bacteria.

Recombinant bacteria according to the invention that are capable of operating at this high temperature are particularly is of high importance in the conversion of the lignocellulosic material into fermentation products. The conversion rate of carbohydrates into e.g. ethanol is much faster when conducted at high temperatures. For example, ethanol productivity in a thermophilic *Bacillus* is up to ten-fold faster than a conventional yeast fermentation process which operates at 30° C. Consequently, a smaller production plant is required for a given volumetric productivity, thereby reducing plant construction costs. As also mentioned previously, at high temperature, there is a reduced risk of contamination from other microorganisms, resulting in less downtime, increased plant productivity and a lower energy requirement for feedstock sterilisation. The high operation temperature may also facilitate the subsequent recovery of the resulting fermentation products.

Hence, in preferred embodiments the recombinant bacterium is capable of growing at a temperature in the range of about 40-95° C., such as the range of about 50-90° C., including the range of about 60-85° C., such as the range of about 65-75° C.

The wild-type bacteria used for preparing the recombinant bacteria according to the invention may be any suitable ethanol producing bacteria, but it is preferred if the bacterium is derived from the division of Firmicutes and in particular from the class of Clostridia.

As mentioned above the present invention is particularly suitable for improving ethanol yields in ethanol producing thermophilic bacteria, and as will be apparent from the following examples, particularly in thermophilic bacteria which are anaerobic bacteria, i.e. bacteria which do not require oxygen for their growth. Thus, the bacteria may in useful embodiments be obligate anaerobes which are bacteria that will die when exposed to atmospheric levels of oxygen. They may also be facultative anaerobes which can use oxygen when it is present, or aerotolerant bacteria which can survive in the presence of oxygen, but are anaerobic because they do not use oxygen as a terminal electron acceptor.

In particular it is preferred if the bacterium is from the class of Clostridia, in particular thermophilic anaerobic bacteria from the order of Thermoanaerobacteriales, such as from the family of Thermoanaerobacteriaceae, including the genus of *Thermoanaerobacter*.

Thus, in accordance with the invention, the bacterium of the genus *Thermoanaerobacter* may be selected from the group consisting of *Thermoanaerobacter acetoethylicus*, *Thermoanaerobacter brockii*, *Thermoanaerobacter brockii* subsp. *brockii*, *Thermoanaerobacter brockii* subsp. *finnii*, *Thermoanaerobacter brockii* subsp. *lactiethylicus*, *Thermoanaerobacter ethanolicus*, *Thermoanaerobacter finnii*, *Thermoanaerobacter italicus*, *Thermoanaerobacter kivui*, *Thermoanaerobacter lacticus*, *Thermoanaerobacter mathranii*, *Thermoanaerobacter pacificus*, *Thermoanaerobacter siderophilus*, *Thermoanaerobacter subterraneus*, *Thermoanaerobacter sulfurophilus*, *Thermoanaerobacter tengcongensis*, *Thermoanaerobacter thermocopriae*, *Thermoanaerobacter thermohydrosulfuricus*, *Thermoanaerobacter wiegelii*, *Thermoanaerobacter yonseiensis*.

In certain embodiments, and as will be apparent from the following examples, the bacterium derived from *Thermoanaerobacter mathranii* may be selected from BG1 (DSMZ Accession number 18280) and mutants thereof. BG1 has previously been described in WO 2007/134607 and is known for its excellent ethanol production capabilities. It is demonstrated in WO 2007/134607, that the base strain BG1 in advantageous embodiments may be modified in order to obtain mutants or derivatives of BG1, with improved characteristics. Thus, in one embodiment the recombinant bacteria according to the invention is a variant or mutant of BG1 wherein one or more genes have been inserted, deleted or substantially inactivated.

As seen in the following examples, it was found by the present inventors, that the ethanol producing capability of BG1 may be significantly increased by insertion of a glycerol dehydrogenase from *Thermotoga maritima* under the control of a xylose inducible promoter into the lactate dehydrogenase region, thereby removing the lactate dehydrogenase gene. The resulting recombinant bacterium was termed BG1BG1.

Thus, in a presently preferred embodiment the recombinant bacterium is *Thermoanaerobacter mathranii* strain BG1G1 which has been deposited in accordance with the terms of the Budapest Treaty on 23 Mar. 2007 with DSMZ—Deutsche Sammlung von Mikroorganismen and Zellkulturen GmbH, Mascheroder Weg 1b, 38124 Braunschweig, Germany under DSMZ accession number 19229.

As shown in the accompanying examples, the insertion of glycerol dehydrogenase leads to a significant NAD+ specific glycerol dehydrogenase activity in extracts from BG1BG1 grown on glucose, in contrast to the wild type bacterium BG1 where no activity is detected.

It was found that not only does BG1BG1 produce close to theoretical yields of ethanol, it also consumes a significant proportion of the added glycerol, thereby enabling production of ethanol from substrates where glycerol is present at less than 50% of the sugar concentration. Since glycerol is typically produced at ethanol production facilities, use of this product could be very favourable. Glycerol could also be purchased from biodiesel production facilities where crude glycerol is available in large amounts. Since only small amounts of glycerol are necessary to enhance ethanol production, a significant amount of impurities in the glycerol can be tolerated.

It is also observed that the ethanol yield of BG1BG1 increases by at least 36% as compared to wild-type BG1 and 15% as compared to a mutant where the lactate dehydrogenase has been deleted without insertion of a glycerol dehydrogenase. It is shown that the expression of the glycerol dehydrogenase is instrumental in this increase in ethanol yield, since no glycerol dehydrogenase enzyme activity or increased yield is observed when the strain is grown in the absence of xylose, where the promoter is not active and the glycerol dehydrogenase gene therefore not expressed.

The following examples also illustrate that in certain embodiments a minimum concentration of 40% (w/w) of glycerol relative to xylose is necessary to obtain the effect, and that an increase of up to 400% (w/w) does not significantly influence the yield. This shows that a large variation in glycerol concentrations can be tolerated, which is of importance for the operational stability if the strains are to be used industrially.

The ethanol yields of wild-type ethanol producing bacteria may in accordance with invention be improved significantly. Thus, in a preferred embodiment there is provided a recombinant bacterium wherein the ethanol production characteristics are enhanced by at least 5%, such as at least 10%, such as at least 15%, such as at least 20%, such as at least 25%, such as at least 30%, such as at least 35%, such as at least 40%, such as at least 45%, such as at least 50%, such as at least 55%, such as at least 60%, such as at least 65%, such as at least 70%, such as at least 75%, such as at least 80%, such as at least 85%, such as at least 90%, such as at least 95%, such as at least 100%, such as at least 150% and such as at least 200%, as compared to a corresponding wild-type bacterium (parental non-recombinant bacterium).

The recombinant bacteria of the invention are, as mentioned above, cultivated in a growth medium comprising glycerol. The exact amount or concentration of glycerol may vary significantly, and it is well within the capability of the skilled person to optimise the ethanol yield by varying the glycerol concentration. In specific embodiments the bacteria are cultivated in a growth medium comprising glycerol in an amount of at least 0.1 g/L, such as at least 0.5 g/L, such as at least 1 g/L, such as at least 2 g/L, such as at least 3 g/L, such as at least 4 g/L, such as at least 5 g/L, such as at least 6 g/L, such as at least 7 g/L, such as at least 8 g/L, such as at least 9 g/L, such as at least 10 g/L, such as at least 15 g/L, and such as at least 20 g/L.

In further embodiments of the invention, the growth medium comprises glycerol in an amount in the range of 1 to 10 g/L, such as the range of 1-8 g/L, such as the range of 1-5 g/L, such as the range of 1-4 g/L.

In some variants, the growth medium comprises carbohydrates selected from the group consisting of monosaccharides, oligosaccharides and polysaccharides.

In some interesting embodiments, one or more additional genes have been inserted and/or deleted in the bacterium.

It may for certain embodiments be desired to insert one or more additional genes into the recombinant bacteria according to the invention. Thus, in order to improve the ethanol yield or the yield of another specific fermentation product, it may be beneficial to insert one or more genes encoding a polysaccharase into the strain according to the invention. Hence, in specific embodiments there is provided a strain according to the invention wherein one or more genes encoding a polysaccharase which is selected from cellulases (EC 3.2.1.4); beta-glucanases, including glucan-1,3 beta-glucosidases (exo-1,3 beta-glucanases, EC 3.2.1.58), 1,4-beta-cellobiohydrolase (EC 3.2.1.91) and endo-1,3(4)-beta-glucanases (EC 3.2.1.6); xylanases, including endo-1,4-beta-xylanases (EC 3.2.1.8) and xylan 1,4-beta-xylosidase (EC 3.2.1.37); pectinases (EC 3.2.1.15); alpha-glucuronidase, alpha-L-arabinofuranosidase (EC 3.2.1.55), acetylesterase (EC 3.1.1.-), acetylxylanesterase (EC 3.1.1.72), alpha amylase (EC 3.2.1.1), beta-amylase (EC 3.2.1.2), glucoamylase (EC 3.2.1.3), pullulanase (EC 3.2.1.41), beta-glucanase (EC 3.2.1.73), hemicellulase, arabinosidase, mannanases including mannan endo-1,4-beta-mannosidase (EC 3.2.1.78) and mannan endo-1,6-alpha-mannosidase (EC 3.2.1.101), pectin hydrolase, polygalacturonase (EC 3.2.1.15), exopolygalacturonase (EC 3.2.1.67) and pectate lyase (EC 4.2.2.2).

Depending on the desired fermentation product, it is contemplated that in certain embodiments it is useful to insert heterologous genes encoding a pyruvate decarboxylase (such as EC 4.1.1.1) or to insert a heterologous gene encoding an alcohol dehydrogenase (such as EC 1.1.1.1, EC 1.1.1.2, EC 1.1.1.71, or EC 1.1.99.8) or to up- or down-regulate an already existing gene (native gene) such as a gene encoding alcohol dehydrogenase.

It is also contemplated that it may be useful in certain embodiments to delete one or more genes encoding phosphotransacetylase and/or acetate kinase.

In one variant of the bacterium of the invention, one or more genes encoding an alcohol dehydrogenase has been inserted. In another variant of the bacterium of the invention, one or more genes encoding a phosphotransacetylase has been deleted. In still another variant of the bacterium of the invention, one or more genes encoding an acetate kinase has been deleted. In still another variant of the bacterium of the invention, one or more additional genes have been up-regulated and/or down-regulated.

It should be understood that the before-mentioned modifications may be combined.

The present invention also provides for an effective method for producing ethanol, comprising culturing a bacterium according to the invention in a growth medium comprising glycerol and a carbohydrate source under suitable conditions.

The carbohydrate source serves as the substrate for the recombinant bacteria according to the invention. In the present context the term "carbohydrate source" is intended to include chemical compounds having the general chemical formula $C_n(H_2O)_n$. Thus, the term "carbohydrate" includes monosaccharides, oligosaccharides and polysaccharides as well as substances derived from monosaccharides by reduction of the carbonyl group (alditols, including sugar alcohols such as glycerol, mannitol, sorbitol, xylitol and lactitol, and mixtures thereof), by oxidation of one or more terminal groups to carboxylic acids, or by replacement of one or more hydroxy group(s) by a hydrogen atom, an amino group, a thiol group or similar heteroatomic groups. It also includes derivatives of these compounds.

The generic term "monosaccharide" (as opposed to oligosaccharide or polysaccharide) denotes a single unit, without glycosidic connection to other such units. It includes aldoses, dialdoses, aldoketoses, ketoses and diketoses, as well as deoxy sugars and amino sugars, and their derivatives, provided that the parent compound has a (potential) carbonyl group. The term "sugar" is frequently applied to monosaccharides and lower oligosaccharides. Typical examples are glucose, fructose, xylose, arabinose, galactose and mannose.

"Oligosaccharides" are compounds in which monosaccharide units are joined by glycosidic linkages. According to the number of units, they are called disaccharides, trisaccharides, tetrasaccharides, pentasaccharides etc. The borderline with polysaccharides cannot be drawn strictly; however the term "oligosaccharide" is commonly used to refer to a defined structure as opposed to a polymer of unspecified length or a homologous mixture. Examples are sucrose and lactose.

"Polysaccharides" is the name given to a macromolecule consisting of a large number of monosaccharide residues joined to each other by glycosidic linkages.

In a presently preferred embodiment, the recombinant bacterium according to the invention is cultivated in the presence of a polysaccharide source selected from starch, glucose, lignocellulose, cellulose, hemicellulose, glycogen, xylan, glucuronoxylan, arabinoxylan, arabinogalactan, glucomannan, xyloglucan, and galactomannan.

Ethanol production from lignocellulosic biomass (i.e. plant materials) has attracted widespread attention as an unlimited low cost renewable source of energy for transportation fuels. Because the raw material cost accounts for more than 30% of the production costs, economically, it is essential that all major sugars present in lignocellulosic biomass are fermented into ethanol. The major fermentable sugars derived from hydrolysis of various lignocellulosic materials are glucose and xylose. Microorganisms currently used for industrial ethanol production from starch materials, *Saccharomyces cerevisiae* and *Zymomonas mobilis*, are unable naturally to metabolize xylose and other pentose sugars. Considerable effort has been made in the last 20 years in the development of recombinant hexose/pentose-fermenting microorganisms for fuel ethanol production from lignocellulose sugars, however, a common problem with genetically engineered ethanologens is co-fermentation of glucose with other sugars, known as "glucose repression" i.e. sequential sugar utilization, xylose conversion starts only after glucose depletion, resulting in "xylose sparing" i.e. incompletely xylose fermentation. Co-fermentation of glucose and xylose is therefore a crucial step in reducing ethanol production cost from lignocellulosic raw materials. Thermophilic anaerobic bacteria have the unique trait of being able to ferment the whole diversity of monomeric sugars present in lignocellulosic hydrolysates. In addition, the industrial use of thermophilic microorganisms for fuel ethanol production offers many potential advantages including high bioconversion rates, low risk of contamination, cost savings via mixing, cooling and facilitated product recovery. These microorganisms are, however, sensitive to high ethanol concentrations and produce low ethanol yields at high substrate concentrations.

As will be apparent from the following examples, the recombinant thermophilic bacterium BG1BG1 of the present invention is capable of producing ethanol on very high dry-matter concentrations of lignocellulosic hydrolysates. In the present context the term "lignocellulosic hydrolysate" is intended to designate a lignocellulosic biomass which has been subjected to a pre-treatment step whereby lignocellulosic material has been at least partially separated into cellulose, hemicellulose and lignin thereby having increased the surface area of the material. Useful lignocellulosic material may, in accordance with the invention, be derived from plant material, such as straw, hay, garden refuse, house-hold waste, wood, fruit hulls, seed hulls, corn hulls, oat hulls, soy hulls, corn fibres, stovers, milkweed pods, leaves, seeds, fruit, grass, wood, paper, algae, cotton, hemp, flax, jute, ramie, kapok, bagasse, mash, distillers grains, oil palm, corn, sugar cane and sugar beet.

In some embodiments, the lignocellulosic biomass material is present in the liquid growth medium at a dry-matter content of at least 10% wt/wt, such as at least 15% wt/wt, including at least 20% wt/wt, such as at least 25% wt/wt, including at least 35% wt/wt.

In further embodiments of the method of the invention, the lignocellulosic biomass material has been subjected to a pre-treatment step selected from acid hydrolysis, steam explosion, wet oxidation, wet explosion and enzymatic hydrolysis.

The pre-treatment method most often used is acid hydrolysis, where the lignocellulosic material is subjected to an acid such as sulphuric acid whereby the sugar polymers cellulose and hemicellulose are partly or completely hydrolysed to their constituent sugar monomers. Another type of lignocellulose hydrolysis is steam explosion, a process comprising heating of the lignocellulosic material by steam injection to a temperature of 190-230° C. A third method is wet oxidation wherein the material is treated with oxygen at 150-185° C. The pre-treatments can be followed by enzymatic hydrolysis to complete the release of sugar monomers. This pre-treatment step results in the hydrolysis of cellulose into glucose while hemicellulose is transformed into the pentoses xylose and arabinose and the hexoses glucose, galactose and mannose. The pre-treatment step may in certain embodiments be supplemented with treatment resulting in further hydrolysis of the cellulose and hemicellulose. The purpose of such an additional hydrolysis treatment is to hydrolyse oligosaccharide and possibly polysaccharide species produced during the acid hydrolysis, wet oxidation, or steam explosion of cellulose and/or hemicellulose origin to form fermentable sugars (e.g. glucose, xylose and possibly other monosaccharides). Such further treatments may be either chemical or enzymatic. Chemical hydrolysis is typically achieved by treatment with an acid, such as treatment with aqueous sulphuric acid, at a temperature in the range of about 100-150° C. Enzymatic hydrolysis is typically performed by treatment with one or more appropriate carbohydrase enzymes such as cellulases, glucosidases and hemicellulases including xylanases.

It was surprisingly found that the recombinant bacterial strain BG1BG1 according to invention is capable of growing in a medium comprising a hydrolysed lignocellulosic biomass material having a dry-matter content of at least 10% wt/wt, such as at least 15% wt/wt, including at least 20% wt/wt, and even as high as at least 25% wt/wt. This has the great advantage that it may not be necessary to dilute the hydrolysate before the fermentation process, and thereby it is possible to obtain higher concentrations of ethanol, and thereby the costs for subsequently recovering the ethanol may be decreased (distillation costs for ethanol will increase with decreasing concentrations of alcohol).

The method of producing ethanol according to invention comprises cultivating the recombinant bacterium in the presence of glycerol. Thus, in preferred embodiments the method comprises cultivating the bacteria in a growth medium comprising glycerol in an amount of at least 0.1 g/L, such as at least 0.5 g/L, such as at least 1 g/L, such as at least 2 g/L, such as at least 3 g/L, such as at least 4 g/L, such as at least 5 g/L, such as at least 6 g/L, such as at least 7 g/L, such as at least 8 g/L, such as at least 9 g/L, such as at least 10 g/L, such as at least 15 g/L, and such as at least 20 g/L. In further embodiments of the invention, the growth medium comprises glycerol in an amount in the range of 1 to 10 g/L, such as the range of 1-8 g/L, such as the range of 1-5 g/L, such as the range of 1-4 g/L.

As shown in the examples, the method in accordance with the invention may in certain embodiments be a fermentation process performed under strict anaerobic conditions, i.e. conditions where no oxygen is present.

The fermentation process may in useful embodiments be conducted in a bioreactor which is operated using a number of different modes of operation, such as batch fermentation, fed batch fermentation or continuous fermentation. The continuous fermentation process may e.g. be performed using a continuous stirred-tank reactor or a continuous upflow reactor.

It may be is of great industrial importance that the ethanol production can run in a continuous operation mode, since downtime due to new start up can be very costly. As shown in the examples, BG1G1 was run in continuous operation mode with ethanol yields as high as 0.47 g ethanol per g substrate (xylose and glycerol) corresponding to 92% of the theoretical maximum yield based on the metabolic pathways of Clostridia. If instead the yield is based solely on the sugar substrate xylose and glycerol is regarded an addition, the maximal yield is 0.55 g ethanol per g xylose corresponding to 108%. This shows the great potential of using recombinant bacteria of the invention for production of ethanol if a favourable source of ethanol is present.

As previously mentioned the recombinant bacterial strain according to the invention may in useful embodiments be a thermophilic bacterium. As shown in the accompanying examples the recombinant bacteria BG1BG1 is a thermophilic and strict anaerobic bacteria which is capable of growing at high temperatures even at or above 70° C. The fact that the strain is capable of operating at this high temperature is of high importance in the conversion of the ligocellulosic material into fermentation products. The conversion rate of carbohydrates into e.g. ethanol is much faster when conducted at high temperatures. For example, ethanol productivity in a thermophilic *Bacillus* is up to ten-fold faster than a conventional yeast fermentation process which operates at 30° C. Consequently, a smaller production plant is required for a given volumetric productivity, thereby reducing plant construction costs. As also mentioned previously, at high temperature, there is a reduced risk of contamination from other microorganisms, resulting in less downtime, increased plant productivity and a lower energy requirement for feedstock sterilisation. The high operation temperature may also facilitate the subsequent recovery of the resulting fermentation products.

Accordingly, the ethanol production method according to the invention is preferably operated at a temperature in the range of about 40-95° C., such as the range of about 50-90° C., including the range of about 60-85° C., such as the range of about 65-75° C.

The method according to invention may further comprise an ethanol recovering step. A number of techniques for ethanol recovery from fermentation broths are known, and these include distillation (e.g. vacuum distillation), solvent extraction (gasoline may e.g. be used as a solvent for the direct extraction of ethanol from a fermentation broth), pervaporation (a combination of membrane permeation and evaporation) and the use of hydrophobic adsorbents.

It is further contemplated that the method according to the invention may further comprise a step wherein surplus glycerol is converted to biogas (e.g. methane generated) which may subsequently be used for generating energy such as heating and electricity.

In accordance with the invention, there is also provided a method for producing a recombinant bacterium having enhanced ethanol production characteristics when cultivated in a growth medium comprising glycerol. The method for producing the recombinant bacterium comprises the steps of transforming a wild-type (parental bacterium) by the insertion of a heterologous gene encoding glycerol dehydrogenase or by up-regulating and already existing native gene of the wild-type bacterium encoding glycerol dehydrogenase. It is also within the scope of the invention to both insert a heterologous gene and up-regulate a native gene in the same bacterium. The method further comprises the steps of obtaining the recombinant bacterium.

EXAMPLES

Materials and Methods

The following materials and methods were applied in the below Examples:
Strains and Growth Conditions Strain BG1 was isolated anaerobically from an Icelandic hot-spring at 70° C. All strains were cultured at 70° C. anaerobically in minimal medium (BA) with 2 g/L yeast extract as in (Larsen et al., 1997) unless otherwise stated. For solid medium, roll tubes (Hungate R E, 1969; Bryant M P, 1972) containing BA medium with 11 g/L phytagel and additional 3.8 g/L $MgCl_2.6H_2O$ was used. For cloning purposes, *Escherichia coli* Top10 (Invitrogen, USA) was used. Top10 was routinely cultivated at 37° C. in Luria-Bertani medium (Ausubel et al., 1997) supplemented with 100 µg/mL ampicillin when needed.

Wet oxidized straw material was prepared using the wet oxidation pretreatment method described by Bjerre et al. (Bjerre et al., 1996) at a concentration of 20% dry solids. The material was added trace metals and vitamins as in BA medium and diluted in water to the final concentration.
Fermentation All fermentation experiments were performed as batch fermentations under strictly anaerobic conditions using 10% (v/v) inoculum. 10 mL of BA media supplemented with 5 g/L glucose/xylose and 2.5 g/L glycerol was used unless otherwise stated. The cultures were grown at 70° C. and the samples were collected after 48 h of growth.

For continuous fermentation in upflow reactors, medium was prepared and supplemented with the same minerals, trace metals, and yeast extract as described above unless otherwise stated. The initial pH of the medium was adjusted to 7.4-7.7 and it was autoclaved at 120° C. for 30 min. To ensure anaerobic conditions, medium was flushed for 45 minutes with a mixture of $N_2/CO_2$ (4:1), and finally $Na_2S$ was injected into the bottle to give a final concentration of 0.25 g/L.

The reactor was a water-jacketed glass column with 4.2 cm inner diameter and 20 cm height. The working volume of the reactor was 200 mL. The influent entered from the bottom of the reactor and the feeding was controlled by a peristaltic pump (Model 503S-10 rpm, Watson Marlow, Falmouth, UK). Recirculation flow was achieved by using an identical peristaltic pump (Model 503-50 rpm, Watson Marlow, Falmouth, UK), with a degree of recirculation to ensure up-flow velocities in the reactor of 1 m/h. The pH was maintained at 7.0 by addition of NaOH (1-2 M), unless otherwise stated. The reactor was loaded with 75 mL of sterilized granular sludge originating from the UASB reactor at Faxe waste water treatment plant (Denmark), and finally the entire reactor system, including the tubing and recirculation reservoir, was autoclaved at 120° C. for 30 min. Before use, the reactor system was gassed for 15 minutes with $N_2/CO_2$ (4:1) to ensure anaerobic conditions and filled with BA medium with initial xylose and glycerol concentrations of 17.5 g/L and 9.7 g/L. The reactor was started up in batch mode by inoculation with 10 mL of cell suspension with an optical density ($OD_{578}$) of 0.9-1. The batch mode of operation was maintained for 48 hours to allow cells to attach and to immobilize on the carrier matrix. After the batch run, the system was switched to continuous mode applying a HRT of 24 hours and an up-flow velocity of 1 m/h.

Analytical Methods

The strains were grown in BA medium without antibiotics in batch for 24-48 hours as stated.

The culture supernatants were analyzed for cellobiose, glucose, xylose, acetate, lactate and ethanol using an organic acid analysis column (Aminex HPX-87H column (Bio-Rad Laboratories, CA USA)) on HPLC at 65° C. with 4 mM $H_2SO_4$ as eluent. The ethanol and acetate measurements were validated using gas chromatography with flame ionization detection. Mixed sugars were measured on HPLC using a Phenomenex, RCM Monosaccharide (00H-0130-K0) column at 80° C. with water as eluent. Mannose and arabinose could not be distinguished using this setup and were therefore tested in separate cultures. Hydrogen was measured using a GC82 Gas chromatograph (MikroLab Aarhus, Denmark).

Enzymes and Reagents

If not stated otherwise enzymes were supplied by MBI Fermentas (Germany) and used according to the suppliers' recommendations. PCR reactions were performed with a 1 unit:1 unit mixture of Taq polymerase and Pfu polymerase. Chemicals were of molecular grade and were purchased from Sigma-Aldrich Sweden AB.

Construction of the Gldh Gene Insertion Cassette

Figure 2:
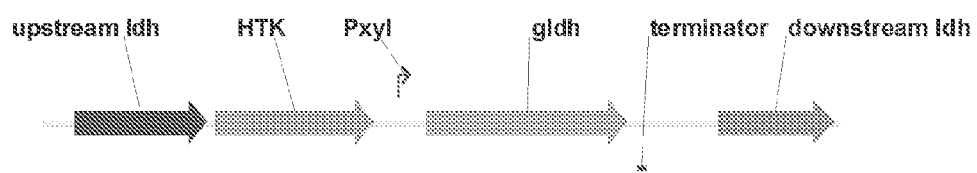
FIG. 2. Schematic presentation of the linear DNA fragment used for replacement of the lactate dehydrogenase of *Thermoanaerobacter* BG1 with a kanamycin resistance cassette and the glycerol dehydrogenase of *Thermotoga maritima*. Upstream ldh and downstream ldh represents the 725 bp and 630 bp regions upstream and downstream of the lactate dehydrogenase of BG1. Pxyl is the promoter transcribing the gldh gene.

The DNA fragment used for insertion of the glycerol dehydrogenase gene from *Thermotoga maritima* into the lactate dehydroganse region of BG1 is shown in FIG. 2 and contains:
1) a DNA fragment upstream of the l-ldh gene of BG1, amplified using primers ldhup1F (SEQ ID NO:18; 5'-TTC-CATATCTGTAAGTCCCGCTAAAG) and ldhup2R (SEQ ID NO:19; 5'-ATTAATACAATAGTTTTGACAAATCC),
2) a gene encoding a highly thermostable kanamycin resistance amplified from plasmid pUC18HTK (Hoseki et al., 1999),
3) an expression cassette composed of a promoter, the complete gldh open reading frame of *Thermotoga maritima* and a rho independent terminator, and
4) a DNA fragment downstream of the l-ldh gene of BG1, amplified using primers ldhdown3F (SEQ ID NO:20; 5'-ATATAAAAAGTCACAGTGTGAA) and ldhdown4R (SEQ ID NO:21; 5'-CACCTATTTTGCACTTTTTTTC). The plasmid p3CH was linearised and electroporated into BG1.

Glycerol Dehydrogenase Assay

The Gldh activity of the tested strain was determined as described below. The tested strains were cultivated in 100 mL of BA media with 5 g/L glucose/xylose and 2.5 g/L glycerol as growth substrate at 70° C. under anaerobic conditions. Cultures at an OD578 of ~0.5 were harvested by centrifugation of 50 mL of the culture at 40,000 rpm and 4° C. for 30 min. The pellet was resuspended in 2 mL of ice chilled extraction buffer composed of 50 mM Tris-HCL, 10% glycerol and 1 mM $MgCl_2$ at pH 8.0. The cells were sonicated for 2 min in an ice bath (Digital Sonifier: Model 250; Branson Ultrasonics Corporation, Danbury, U.S.A.). The sonicated cells were centrifuged at 20,000 g and 4° C. for 30 min. The supernatant was used for Gldh activity assay at 70° C. and pH 8.0 using the continuous spectrophotometric rate determination method as previously described (Burton, R. M.; 1955). One unit was defined as the amount of enzyme that produced 1 µmol of NADH per minute at 70° C. and pH 8.0. Total concentration in the cell extracts was routinely measured by the Bradford method (Bradford, M. M., 1976) using bovine serum albumin (BSA) as a standard.

Calculations

A significant loss of ethanol is observed when fermentations are performed at 70° C. with no condensation of the gas phase. To take this loss into account, the following formula was $$\text{used } CR(\%) = \frac{3(C_{EtOH}/M_{EtOH} + C_{Ace}/M_{Ace}) + C_{BM}/M_{BM}}{5C_{Xyl}/M_{Xyl} + 3C_{Gly}/M_{Gly}} \times 100:$$

where $C_i$ is the concentration of compound i, i.e. substrate consumed or product produced (g/L) and M, is the molecular weight of compound i (g/mol). Lactic acid production was below the detection limit of 0.2 g/L and was therefore not included in the calculations. A biomass yield of 0.045 g/g was assumed based on experiments with thermophilic Clostridia (Desai et al., 2004; Lynd et al., 2001). For carbon recovery calculations it was assumed based on the Clostridial catabolism of xylose that 1 mole of $CO_2$ is produced per mole of ethanol or acetate (Desai et al., 2004; Lynd et al., 2001). It is also assumed that no other products are formed. This assumption is reasonable, since a carbon recovery of close to 100% (SD±2%) is seen in closed batch fermentations, where no ethanol loss occurs.

Example 1

Construction of BG1 G1

Figure 3:
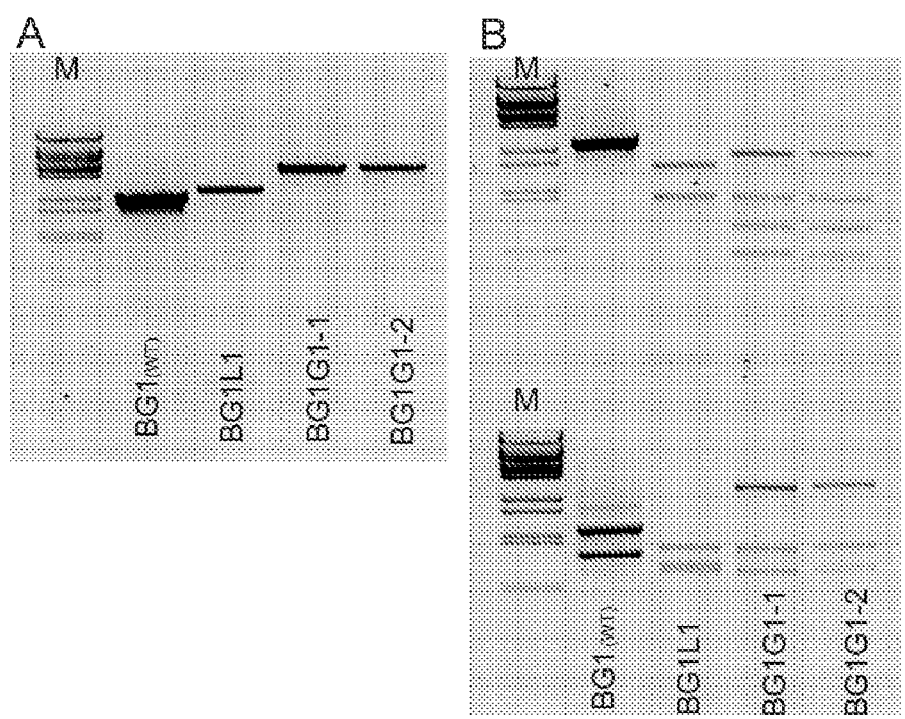
FIG. 3. PCR analysis of two independent BG1G1 clones. A) PCR on chromosomal DNA from BG1, BG1L1, and two BG1G1 clones using external lactate dehydrogenase region primers. B) Restriction analyses of the fragments shown in A using restriction enzymes EcoRI (upper part) and PstI (lower part).

The lactate dehydrogenase of BG1 was replaced by a kanamycin resistance gene and a glycerol dehydrogenase from *Thermotoga maritima* using the fragment shown in FIG. 2. The resulting clones were checked by PCR using primers annealing outside the region using for homologous recombination. In this way, ldh loci in which no recombination have taken place will also be amplified although the fragment will be of different length (FIG. 3A). The PCR fragments obtained were digested with the restriction enzymes EcoRI and PstI (FIG. 3B). The resulting fragments were found to be of the expected lengths, showing that pure correct clones had been obtained. To further confirm the identity of the clones, the PCR products were sequenced. The sequences were identical to the predicted sequences of the recombinant clones.

To confirm that a glycerol dehydrogenase had indeed been inserted under the control of the xylose isomerase promoter Pxyl, studies of glycerol dehydrogenase activity in cultures grown on glucose and xylose were performed. The results are shown in the below Table 1.

TABLE 1

Specific NAD+ dependent Gldh activity of
T. BG1 wild type and mutant strains of L1 and G1

| Strain | Activity (U/mg) | |
|---|---|---|
| | Glucose | Xylose |
| BG1 | ND | ND |
| BG1L1 | ND | ND |
| BG1G1 | ND | 0.438 ± 0.04 |

Note.
One unit is defined as the amount of enzyme that produced 1 μmol of NADH per minute at 70° C. and pH 8.0. Values shown are average of triplicates from anaerobic cultures.
ND: not detected (less than 0.001 U/mg).

As Table 1 shows, no glycerol dehydrogenase activity was detected in wild type BG1 or in BG1L1 grown on glucose or xylose. Also, no glycerol dehydrogenase activity was detected when BG1G1 was grown on glucose, where the Pxyl promoter is repressed. Only when BG1G1 was grown on xylose, glycerol dehydrogenase activity was detected showing that the gene had been correctly inserted and that it was under the control of the Pxyl promoter.

Figure 4:
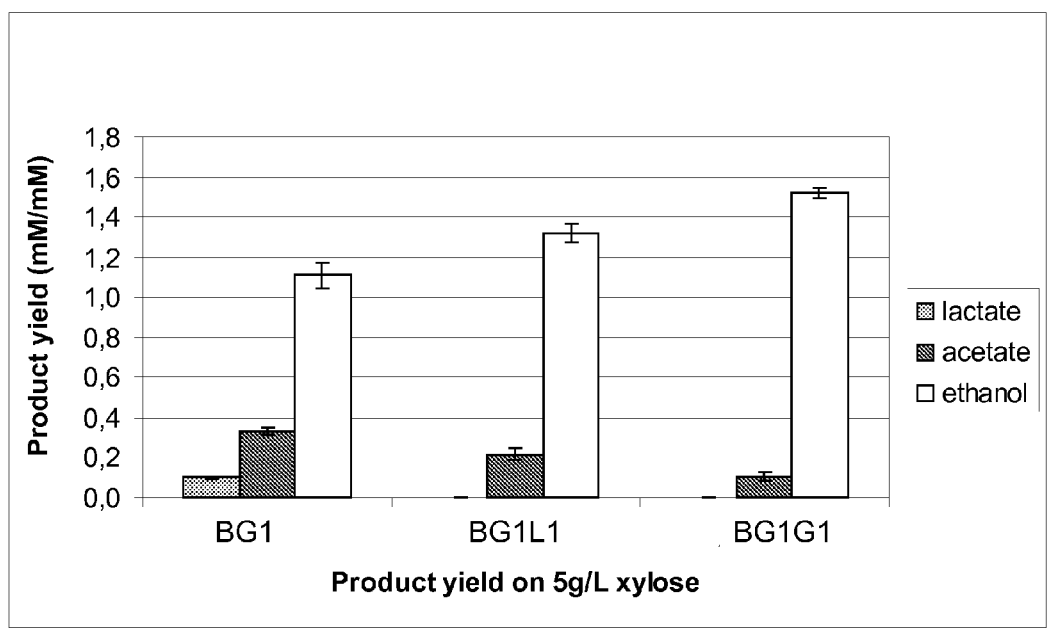
FIG. 4. Product yield of BG1G1 compared to the parent strain BG1, and to the parent strain with a lactate dehydrogenase deletion (BG1L1, DSM Accession number 18283). Fermentations were performed in batch.

BG1, BG1L1 and BG1G1 were grown on BA medium with 5 g/L xylose and 5 g/L glycerol in batch. When xylose is present in the medium, the Pxyl promoter transcribing the gldh gene will be active, and Gldh enzyme will be produced. The GLDH oxidizes the glycerol present in the medium to glycerone with concomitant reduction of NAD+ to NADH+ H+. As can be seen from FIG. 4, BG1G1 has a significantly higher yield of ethanol under these conditions as compared to the wild type BG1 or the lactate dehydrogenase deficient mutant BG1L1.

The Increased Expression is Dependent on Expression of the Gldh Gene

Figure 5:
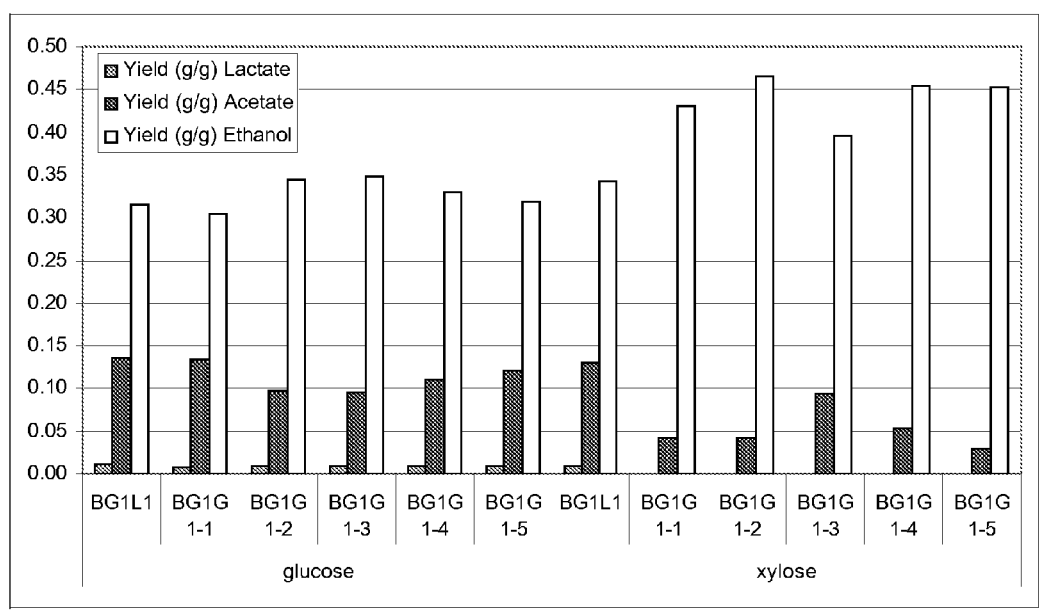
FIG. 5. Product yield of five independent clones of BG1G1 compared to the parent strain with a lactate dehydrogenase deletion (BG1L1). Fermentations were performed in batch.

FIG. 5 shows the ethanol yields of BG1L1 and five independent clones of BG1G1 grown on either glucose or xylose. When no xylose is present, the Pxyl promoter will not transcribe the gldh gene, and therefore much less GLDH protein will be present. GLDH enzyme assays supported this finding. As expected, ethanol yields were much lower when glucose was used as carbon source, showing that it is indeed the GLDH protein which is responsible for the increased ethanol yield.

Example 4

Optimization of Glycerol Concentration

Figure 6:
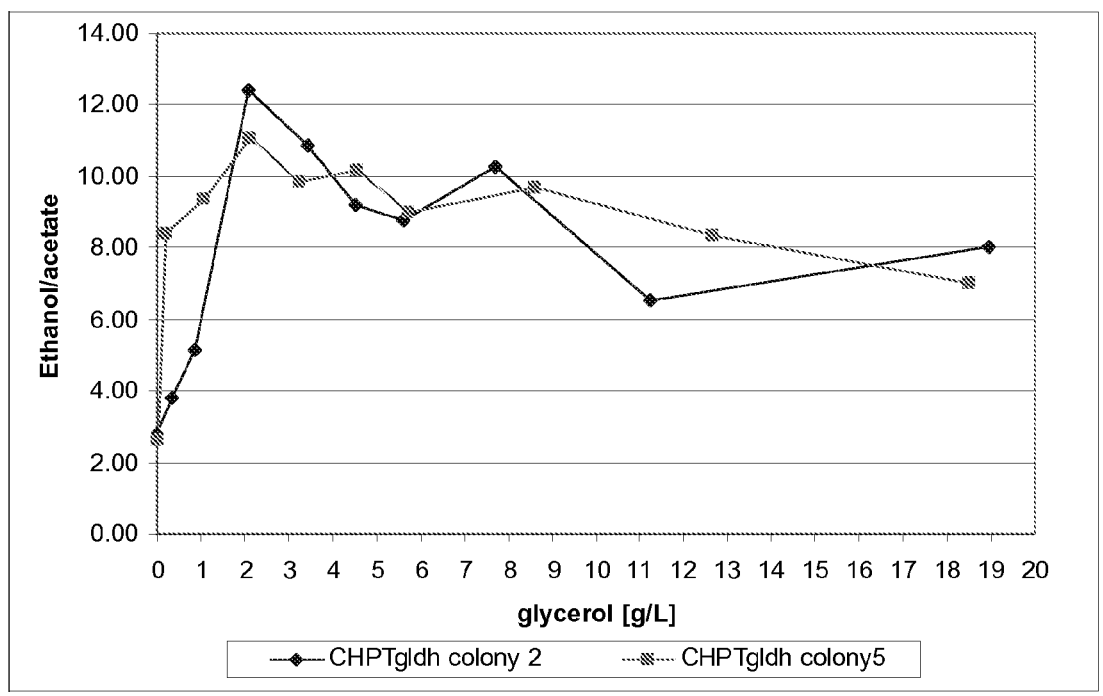
FIG. 6. Ratio of ethanol over acetate produced by two independent clones of BG1G1 as a function of concentration of glycerol in the growth medium.

FIG. 6 shows the ratio of ethanol to acetate produced in batch experiments with two independent clones of BG1G1 using xylose as carbon source and with varying concentrations of glycerol. As can be seen, the highest ethanol yields are obtained with glycerol concentrations from approximately 1 to 9 g/L of glycerol in the medium. At higher concentrations, lower ethanol yields are seen, probably due to stress caused by shortage of NAD+, which is necessary for glycolysis.

Example 5

Growth on Wet-Oxidized Wheat Straw

To test if BG1G1 was able to grow in the harsh conditions of wet-oxidized wheat straw (WOWS), batch experiments with up to 10% dry matter WOWS were performed. BG1G1 was able to grow at all concentrations of WOWS, showing that the strain had maintained the ability of BG1 to produce ethanol at high yields in this material. The highest ethanol to acetate ratio was 9.5 g/g.

Example 6

Growth of BG1G1 in Continuous Culture

Higher ethanol productivities can be obtained if continuous immobilized reactor systems are used. Furthermore, many thermophilic anaerobic bacteria have low tolerance to high sugar concentrations, a problem that can be overcome with the use of continuous fermentation systems. BG1G1 was grown in a continuous upflow reactor to show that high yields of ethanol could be produced in this type of reactor.

Figure 7:
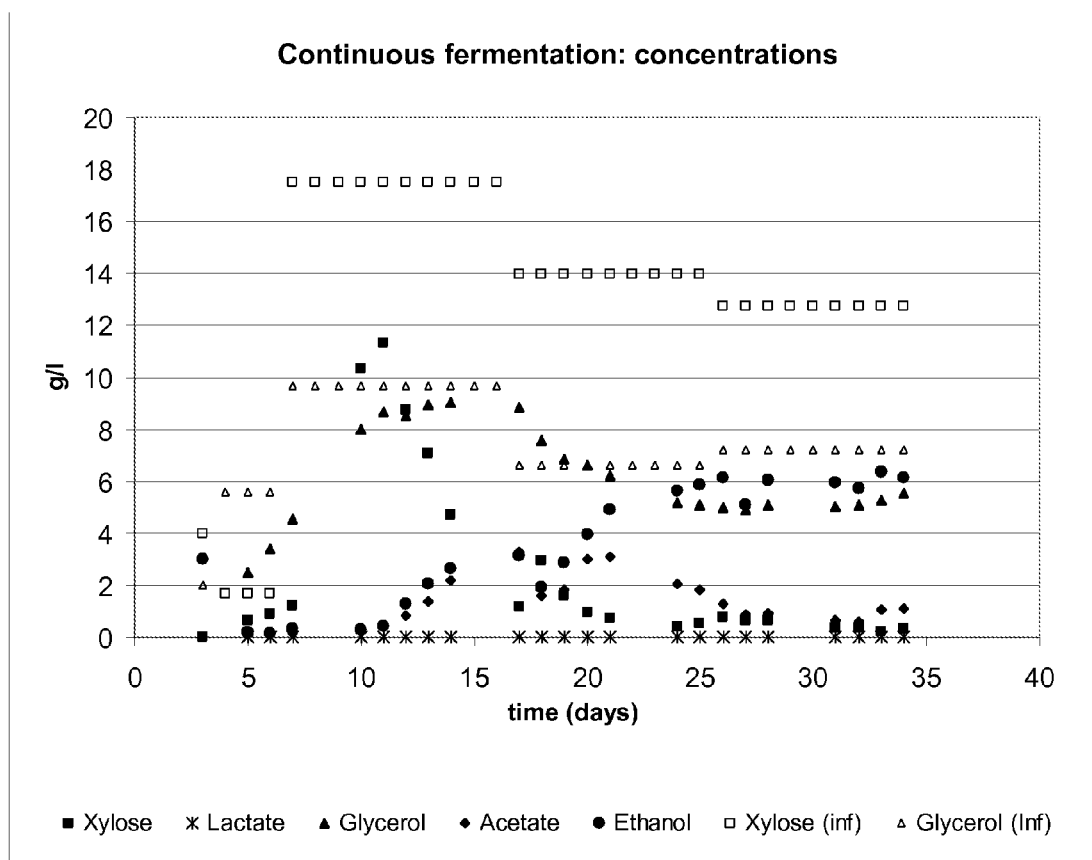
FIG. 7. Concentrations of different compounds in the influent (open symbols) and inside the reactor (closed symbols) from a continuous fermentation of mixtures of xylose and glycerol in an upflow reactor.
Figure 8:
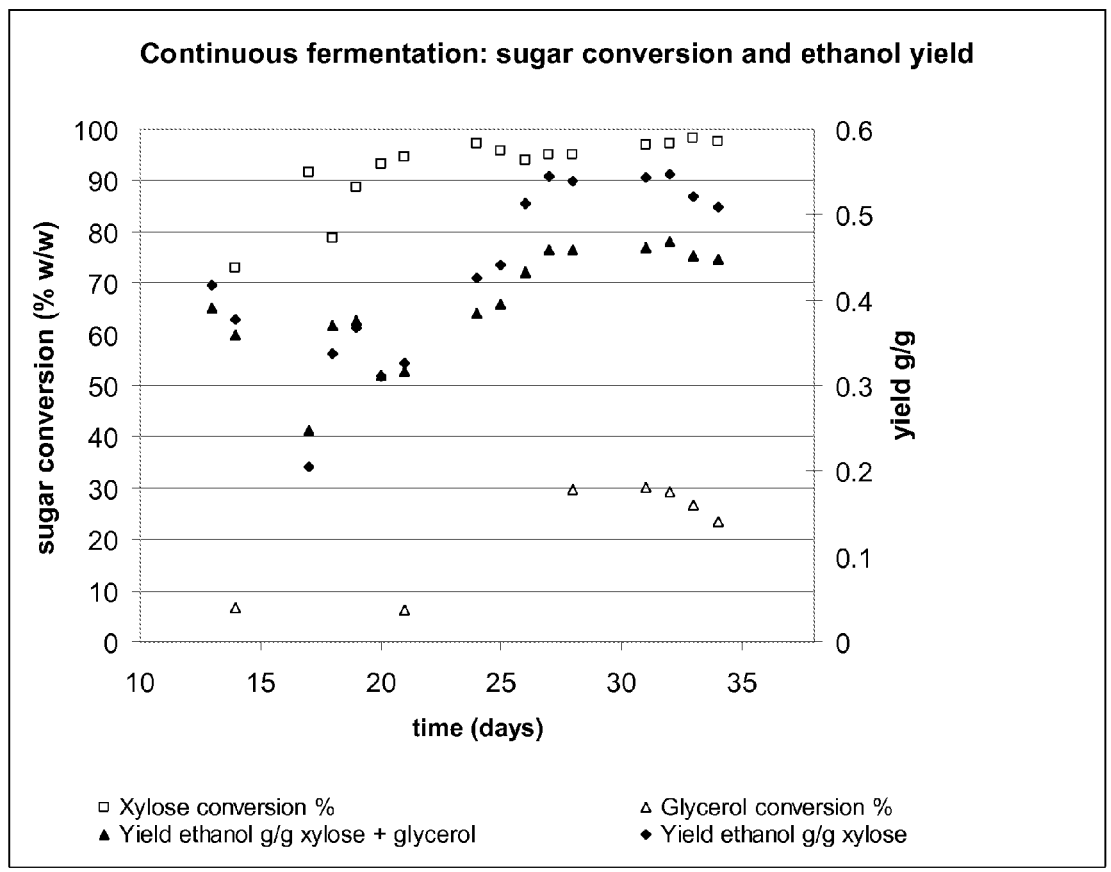
FIG. 8 illustrates the sugar conversion and the ethanol yield (g/g) in the continuous fermentation.

As FIG. 7 shows, steady state was obtained after 27 days at xylose and glycerol concentrations of 12.8 g/L and 7.2 g/L, respectively. At this stage almost all sugars were consumed and no lactic acid was detected. The highest ethanol yield, of 0.47 g ethanol per g of xylose and glycerol consumed, corresponding to 92% of the maximal theoretical yield, was observed after 32 days during growth on 12.8 g/L of xylose and 7.2 g/L of glycerol. If the ethanol yield is based solely on the consumed xylose, a yield of 0.55 g ethanol per g consumed xylose or 108% of the theoretical yield. Therefore, the introduction of the glycerol dehydrogenase not only increases the ethanol yield from the substrate sugars, it also enables the use of glycerol as a substrate. This clearly shows that using a strain which constitutively express a glycerol dehydrogenase is a clear advantage if glycerol can be purchased at a favourable price. Glycerol not consumed in the fermentation can favourably be converted to biogas, thereby further increasing value of the process. FIG. 8 illustrates the sugar conversion and the ethanol yield (g/g) in the continuous fermentation.

The invention claimed is:

1. A thermophilic recombinant bacterium comprising a heterologous gene encoding a glycerol dehydrogenase, wherein the heterologous gene encoding a glycerol dehydrogenase has been incorporated into the chromosome of the bacterium, and is inserted into:
- a lactate dehydrogenase encoding region of said bacterium,
- a phosphotransacetylase encoding region of said bacterium, or
- an acetate kinase encoding region of said bacterium; and
wherein said heterologous gene encoding a glycerol dehydrogenase is obtained from the *Thermotoga* group or the *Geobacillus* group of bacteria.

2. A bacterium according to claim 1, wherein the inserted heterologous gene is encoding a glycerol dehydrogenase selected from the group consisting of Glycerol dehydrogenase (E.0 1.1.1.6); Glycerol dehydrogenase (NADP(+)) (E.C. 1.1.1.72); Glycerol 2-dehydrogenase (NADP(+)) (E.C. 1.1.1.156); and Glycerol dehydrogenase (acceptor) (E.C. 1.1.99.22).

3. A bacterium according to claim 1, wherein the heterologous gene encoding a glycerol dehydrogenase is obtained from the *Thermotoga* group of bacteria.

4. A bacterium according to claim 1, wherein the heterologous gene encoding a glycerol dehydrogenase is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 and SEQ ID NO:17.

5. A bacterium according to claim 1, wherein the heterologous gene encoding a glycerol dehydrogenase is inserted into the lactate dehydrogenase encoding region of said bacterium.

6. A bacterium according to claim 1, wherein said heterologous gene encoding glycerol dehydrogenase is operably linked to an inducible, a regulated or a constitutive promoter.

7. A bacterium according to claim 1, wherein the bacterium is obtained from the genus of *Thermoanaerobacter*.

8. A bacterium according to claim 7, which is obtained from the *Thermoanaerobacter mathranii* strain selected from BG1 G1(DSMZ Accession number 18280).

9. A bacterium according to claim 7, which is of the *Thermoanaerobacter mathranii* strain BG1G1 (DSMZ Accession number 19229).

10. A bacterium according to claim 1, having increased ethanol yield from xylose when cultivated in a growth medium comprising glycerol and xylose as compared to parental bacterium.

11. A method for producing ethanol, said method comprising the steps of culturing a bacterium according to claim 1 in a growth medium comprising glycerol and a carbohydrate source under suitable conditions, wherein the carbohydrate source is selected from the group consisting of a monosaccharide, an oligosaccharide and a polysaccharide.

12. A method according to claim 11, wherein the carbohydrate source is a polysaccharide selected from the group consisting of starch, lignocellulose, cellulose, hemicellulose, glycogen, xylan, glucuronoxylan, arabinoxylan, arabinogalactan, glucomannan, xyloglucan, and galactomannan.

13. A method according to claim 11, which is a fermentation process performed under strict anaerobic conditions.

14. A method according claim 11, which is a continuous fermentation process.

15. A method according to claim 11, wherein the growth medium comprises a concentration of 40% up to 400% (w/w) of glycerol relative to xylose.

16. A method for producing a recombinant bacterium having increased ethanol yield from xylose when cultivated in a growth medium comprising glycerol and xylose as compared to parental bacterium, said method comprising
(a) transforming a parental thermophilic bacterium by the insertion of a heterologous gene encoding glycerol dehydrogenase into the chromosome of the bacterium; and
(b) obtaining said recombinant bacterium,
wherein said heterologous gene encoding a glycerol dehydrogenase has been inserted into:
- a lactate dehydrogenase encoding region of said bacterium, a phosphotransacetylase encoding region of said bacterium, or
- an acetate kinase encoding region of said bacterium; and
wherein said heterologous gene encoding a glycerol dehydrogenase is obtained from the *Thermotoga* group or the *Geobacillus* group of bacteria.

* * * * *

UNITED STATES PATENT AND TRADEMARK OFFICE
CERTIFICATE OF CORRECTION

PATENT NO. : 8,236,547 B2  Page 1 of 1
APPLICATION NO. : 13/055079
DATED : August 7, 2012
INVENTOR(S) : Marie J. Mikkelsen et al.

It is certified that error appears in the above-identified patent and that said Letters Patent is hereby corrected as shown below:

Col. 37, line 38,
Please correct in claim 2, line 4 "E.O." to "E.C."

Col. 37, lines 61 and 62,
Please correct claim 8, delete the words "selected from" and "G1"

Signed and Sealed this
Twenty-third Day of October, 2012

David J. Kappos
*Director of the United States Patent and Trademark Office*

SEQUENCE LISTING

<160> NUMBER OF SEQ ID NOS: 21

<210> SEQ ID NO 1
<211> LENGTH: 1095
<212> TYPE: DNA
<213> ORGANISM: Thermotoga maritima

<400> SEQUENCE: 1

```
tcaagtgagg ttttttctca tccttccgta cctgtctgct gcttttaggg cgaaaaacac      60
atcctttgat gtcacaggtt ggggttcgtt gtgtattgtt tcattcttgt cacaggcttt     120
ctcagccact ttcatcagat cctcgtccga aacaccatca agtcctatct ctgccagagt     180
```

```
agtgggtaat cccacttctt cacagaagga gtagacctct tcgatcatct ttctgggttt    240
gtcagtcaaa aacagtgatg cgagaactcc tatggccact ttttcccgt gtaaatactt    300 gtgggtattt tccagaacgg tgagaccgtt gtgaatagca tgtgcagctg ccagtcctcc   360
actttcgaat cccagaccac ttaaaagggt gttcgcctca acgattttt caagggcagg    420 tgtgacagac ttttcctcca ccgacctttt cgcaagtaca ccgtattcta gaagtgtctc   480
atagcaaagt cttgcgagcg cgtaggctgt catcgaacca agtcttcccg tcatatttgg   540
agcgtatttc tgtttacaag attctgcctc aaaccacgtg gcaagggcat ctcccattcc   600
ggcaacaaga aacctcgcgg gggctttcgc cacaatctcc gtgtctacca gaacgacatc   660
tggattcctt ggcaaaaaca ggtatctttt gaattcccccg tttggtgtgt aaatcacgga   720
aagggcgctg catggagcat ctgtagaggc aatagttgga caatcacaa caggctttt    780 caacttatag gcgaccgctt tagcggtatc gagtgtttt ccgccaccta tgcccaccac    840
cacgtctgtt tcttcttcaa caagacctga agtcgctct atctcttcgt ctgaacactc    900
tccaccaaag atctgtttgt ttaccctgac ttttgtgaaa gagctgaaga aattttctcc   960
tagcacgttt ttgtccacaa aatcatcgat caccacaaat gcccttttctc caaaacgaga   1020 aagttcttct tctagaatgt tgatagcacc tgcccccctga acatatctac ctggaaatat  1080
ggtggttgtt atcat                                                    1095

<210> SEQ ID NO 2
<211> LENGTH: 1104
<212> TYPE: DNA
<213> ORGANISM: Escherichia coli

<400> SEQUENCE: 2
ttattcccac tcttgcagga aacgctgacc gtactggtcg gctaccagca gagcggcgta    60
aacctgatct ggcgtcgcgc cgccaggcat gttgtgaatg gtttcacctt ctgcacatgc   120
cgcttctgcc acaattcgca ttttcgccgg gacatcttct ttaatatcca gttgagcgag   180
agttattggc aaacctaccg catggctaag ggcagctacg gtttcgattt cctccaccgg   240
cgcattttcc agaaccagct gcgtcagcgt accgaatgcc acttttttcac cgtgataata   300 gtgatgcgcg tccgggatag cggtcaggcc gttatgcact gcgtgcgccg cagccagacc   360
accactttca aaaccaacac cgctcaaata ggtgttcgct tcaatcacgc gctccagcgc   420
cggagtcact acatgctgtt cggcagcaag catcgctttt tcgccttctt ccagcagggt   480
gttgtagcac agttcagcca gtgccagcgc agcctgggtg cacttgccgc ccgccatggt   540
ggtcgcgccg ctacgagagc aggcacgcgc ttcaaaccag gttgccagcg catcgccgat   600
acccgccgct aacagacgtg caggtgcgcc agcgacgatt ttggtgtcga caatgaccat   660
attcgggtta tttggcaaca gcagatagcg gtcaaactca ccctcatcgg tgtagataac   720
agacaatgcg ctgcacggtg catcggtaga ggcgatagtc ggtgcgatcg ctaccggaac   780
acccatgaaa tgtgccagtg ctttggcagt atcgagggtt tttccgccac cgataccgag   840
aattgcgcca cactgcgcag tctccgcgat gccacgcaga cggtcgatct cattttgcga   900
acattcaccg ccaaacggcg caatttctac taccagtcca gcatctttaa agcttttctc   960
gacagtggat tgagcaaaac ctaaaacaaa tttgtcaccc accactaacc agcgttctgc  1020
cagcggcttc aggtattcgc ccagacgatt aatcacatca gcgccctgga tgtatttacc  1080
cggtgattga ataatgcggt ccat                                         1104
```

```
<210> SEQ ID NO 3
<211> LENGTH: 1104
<212> TYPE: DNA
<213> ORGANISM: Salmonella typhimurium

<400> SEQUENCE: 3
ttattcccat tcctgcaaga agcgttgacc gtactggtcg gcgaccagca gcgcggcgta      60
cacttcatcc ggcgttgcgc cgccaggcat gttatgaata gtttcacctt ctgcgcagga     120
ggcttccgcg acggtgcgca tcttggccgg aatatcctgt ttaatatcca gttgcgccag     180
cgtaatcggc aggccaacgg aatggcacag cgccgcaacg gtttcgattt cttcgaccgg     240
cgcgttttcc agcaccagtt gcgtcagcgt accgaaagcg accttctcac cgtgataata     300
gtggtgcgca tccggaatcg ccgttaaacc gttatgaatc gcgtgcgctg cggccagacc     360
gccgctttca aaaccgaccc cgctcaggta ggtgttggct tcgatgacgc gttccagcgc     420
tggcgtgacg acgtgctgtt cggcggccaa catggctttt tcgccttctt cgatcagcgt     480
gttatagcat agctccgcca gcgccagcgc ggcctgtgta cacttgccgc cgccattgt      540 ggtggcgccg ctgcgtgagc aggcgcgcgc ttcaaaccag gtcgccagtg catcgccgat     600
accggctgcc agcagacgcg ccggcgcgcc cgccactatc tgcgtatcga caataaccat     660
attcgggtta tgcggcagca gcagataacg gtcaaactca ccggcatcgg tataaataac     720
cgagagtgcg ctgcacggtg cgtcggtaga ggcgatggtc ggcgcgatag cgaccgggac     780
gttcataaag tgcgccagcg cttttggcggt atccagcgtt ttaccgccgc cgatacccag     840
tacggcgcca cactgacttt tttcggcgac ggcgcgcagc ctgtcgatct cattttgcga     900
acattcgccg ccaaacgggg cgatttctac tgacaaaccg gcatccgtca ggcttttgcg     960
cagcgtctct tcggcaaatc ccagcacgaa tttatcgccc acaaccagcc agttgttcgc    1020
cattggtttt aaataatcgc caagacgcgc gatgacgttt gcaccctgaa tatacttacc    1080
tggtgactga ataatgcgat ccat                                           1104

<210> SEQ ID NO 4
<211> LENGTH: 1092
<212> TYPE: DNA
<213> ORGANISM: Clostridium botulinum

<400> SEQUENCE: 4
ttatgataag gattgtccaa gtgcatctgc tgcaagtata gctgcgtata catcattagg      60
agtgacttca aaaggcatat tatatattgt ttctccttct gcacaagatg ttttggatac     120
ttccataagc ttttcttcat ttatttcatt aattccaagt tgttttaaag ttacaggaag     180
accaagttct atacaaaatt ctaagacttc ttgaatttct tccattggac tgttttcaag     240
tattaattga actattgtac caaaagctac ttttttctcca tgatataagt gatgacattc     300
ttcaagaact gtaaaaccat tatgaatagc atgagcagct gcaaggccag cactttcaaa     360
tcctattcca cttaaataag tattagcttc tacaatattc tctactgctt ttgtacatac     420
cttcttttca actgcaagtt tagctttcaa gccatcttca ataagagttt cataacaaag     480
agttgcaagt gctaaggcag ctttttgttat tttcccacca gacatattat tcgcatttgc     540
ttttgcacaa gctctagctt caaagaatgt tgcaagtgca tcacccatac cagctactaa     600
aagtcttgct ggggctttag atataatttc tgtatccatt aaaactatat ccggattttt     660
aggaagaagt atgtattcac taaaagttcc gtcttcagta taaataacag ataaagcact     720
acaaggtgca tctgtggaag ctatagttgg aacaataaca acaggagatt ttcataata     780 agataccgct ttagctgtgt ccaagatttt tccgccacca acaccaacta caacatcaca    840
```

-continued

| | |
|---|---:|
| attattttca gcacaaactt tttttagtct ttcaatttca ttatgggaac attcaccatt | 900 |
| aaagatttca aaagttattt ttgaattagt gttttcaaag cttttcttta ttacatcacc | 960 |
| tgttctttta aagccacttt tactcactat aaataaaaat gattttccaa gattacctat | 1020 |
| gtgatcataa atttttttta attccccatt accttgtaca tattttgaag gtgaaataat | 1080 |
| tattttttgcc at | 1092 |

<210> SEQ ID NO 5
<211> LENGTH: 1089
<212> TYPE: DNA
<213> ORGANISM: Vibrio vulnificus

<400> SEQUENCE: 5

| | |
|---|---:|
| atgttaacaa caactatatt tccaggtcgt tatgttcaag gtaaagatgc tcgaaaacaa | 60 |
| cttggagtag aactcaatcg ttttggaaaa aaggtctaa tgatctgtga ctcatttgtt | 120 |
| tatgatacat tattttctga gtttgaacct tatcttgaga ccgttgaagt tgaagtgatc | 180 |
| cggtttgcta gtgaatgttg tgacgaagaa ataacacgtc tgacagccat gttgaaaaat | 240 |
| tttgagggtg aatttgtggt tggattaggt ggaggaaaaa ccattgatac agcaaaagca | 300 |
| acctcgtatg aagcgagagt ccctgtggca attgtgccga cttttggcagc gagcgatgca | 360 |
| ccatgcagtg cactatccgt tatttacact caagaaggag agtttaagcg ttatcttttc | 420 |
| ctgcctcaaa atccgaatct tgtcttggtc gacacacaaa ttattgccaa ggcacctgtt | 480 |
| cgattcctta tagctgggat cggtgatgcg ctagcaacat ggtttgaagc agaatcatgc | 540 |
| cagcaaagtt ttgcctcgaa tatgacaggt tatatgggtt cattgtcagc atatgcgtta | 600 |
| gcacgtttgt gttacgacac tttgcttgaa tacggcgtaa tagctaaaac atcgaatgaa | 660 |
| caaggtgtgg ttactccagc gctcgaacgt gttgtggaag caaatacgtt gcttagtgga | 720 |
| ttaggtttcg aaagtggtgg tcttgctgct tctcatgcga ttcataatgg tttaacagta | 780 |
| ttggagccaa cacatgtgtt tttgcatggt gaaaaagtcg catttggttt gctttcttct | 840 |
| ctattcctta ctgataaacc agcacagacc atcgcaactg tttatgactt ctgcgaaaaa | 900 |
| gttggcttgc caacgactct gtctcaaatc ggtttagaaa atgtatccga tgaagattta | 960 |
| ttggcagtgg ctgaagcttc atgtgcagaa ggtgagacca tccacaacga acctcgaact | 1020 |
| gtaactccag atatggtgtt tgcagcaatg aaagcggcaa atgtagaagg gttacgtcgc | 1080 |
| aagagctaa | 1089 |

<210> SEQ ID NO 6
<211> LENGTH: 1101
<212> TYPE: DNA
<213> ORGANISM: Clorobium ferrooxidans

<400> SEQUENCE: 6

| | |
|---|---:|
| atgctgcaga aggctttgtt tccgggcaag tatatccagg gcgcaggggc tctcggagag | 60 |
| ttgccggctc ttgtcaggct ctttggcaac aggggatga ttcttgcttc tccttctgtt | 120 |
| tatactgccg ttcttcctga gagcgggctc gatctgaagg gcagttcgct gcaagcagaa | 180 |
| cgattcggcg gggagtgcag tgaaaaggag ctgtcgaggg tggctgcact tattgcggag | 240 |
| aacagggcg atgtgcttgt cggcatggga ggcggcaaaa caattgatac ggcgaaaatt | 300 |
| gctgctgacc gggcggggat tccggttatt attgtgccga ccatcgcctc cactgacgcg | 360 |
| ccgtgcagcg gttgtgccgt tatctacact gaagaggggg tgtatgaatc ggcctgctat | 420 |
| cagaaatcca atccggcagc cgtgctggtg gataccgaaa ttattgcaaa agcacccgtt | 480 |

```
cgttttcttg ttgccggtat gggcgatgca ctggcgacct ggttcgaggc aaactcatgc      540
agcaggacac aatcatcaaa cgagtgcggc ggcctcagca ccctgaccgg gctcagcctc      600
gcaaggctct gttatgatac gcttattcaa tatgggccga gcgcaagaat agctgccaag      660
cagcacatca taacaccagc tctggagcat attgtggagg ccaatattct gctcagtgga      720
gtcggttttg agagtggcgg tcttgcaagt gcccactcca ttcacaacgg tcttacggca      780
ctggctgaaa cacacgcctt taccacggga gagaaggtgg cttccggttt gcttgcaggc      840
cttcagctca ctgatgcctc gccggatgta tcggagcagg tctacgcttt ttgtgaggag      900
gtaggccttc caaccaccct tgccgatatc ggtcttcgtg atttcgaccg tgaacgattg      960
atgcctgccg cagtaaaagc ctgtgcaccc gctgaattca ttcatcacga agcgggcagc     1020 atcaccccg aaaaagtcct tcaggccatg ctcatggctg acgctatcgg agcatcgaga     1080
aaaaagaggc aaaacgcata g                                               1101

<210> SEQ ID NO 7
<211> LENGTH: 1092
<212> TYPE: DNA
<213> ORGANISM: Geobacter Lovleyi

<400> SEQUENCE: 7
atgctgaaca aagcgatgtt ccccggaaaa tacctgcaag gcgcagcggc tctgaacgag       60
ttgccggccc tggtccaact gtttggcaga cagggcctga tcctggcttc ggcaacggcc      120
tgcgacagga ttcttcctga cagcggcatc gacctgaagc gacataatct gtcgctcgaa      180
cgttttaacg gcgagtgttg cgaacaagag ctgacccgcc tggcagccgt cattaaagca      240
aagcaggtgg atgtcctggt ggggatgggt ggcggcaagg ccattgacac ggcaaagatt      300
gcagccgacc gtgccggcat cccggtcatc atcgtaccca ccatcgcctc caccgacgct      360
ccctgcagcg gctgcgccgt gctgtattca gcacagggtg tctttgaatc ggtttactac      420
cagcgctcaa acccggcagc tgtgctggtg gactccgcca tcatcgtccg ggcgccggtc      480 cgcttttctgg tggccggcat gggagatgcg ctggcaacct ggtttgaggc ccgttcctgc      540
catgccaccc gttcggcaaa cgcctgcggc ggtctcagta ccctgaccgg ccttaacctg      600
gcccggctct gctacgatac cctgctgcgc tacggcgcgg ccgccaagac cgcagcggag      660
caacagatca tcaccccggc cctggagcat atcattgagg ccaacaccct gctttccggc      720
atcggctttg aaagcggcgg actggccagc gcccattcca tccacaacgg actgaccgca      780
ttggcagaaa cccatgcctt ctaccacggt gagaaagtgg cctttggtct gttggccggt      840
ctgcagttga tcgacgcacc gccggaagag atcaacgaag tctacaggtt ctgtgaggca      900
gtggggttgc ccaccaccct ggcggctgtc ggcctggccg gatgcggacg cgatcgcctg      960
ctgcaggtgg cacagaaggc ctgcgcccccg gaggagtgca ttcaccatga ggcaggtagc     1020
atcacgcctg acaaggtgct taacgccatg ctggcggcag atgcgatcgg cacacgcaga     1080
aaatcagtgt ga                                                         1092

<210> SEQ ID NO 8
<211> LENGTH: 1098
<212> TYPE: DNA
<213> ORGANISM: Ruminococcus gnavus

<400> SEQUENCE: 8
ttactctccg agaaaataat gtccgtatgc atctgccgcc ttgatcgcat ctgccacttt       60
cttcggtgtc acttcaaacg gcatattgtg cagagtatct gtctcggcac aggctgcctc      120
```

```
tgccactttc atcaactgtt cttccgtaat cttacctgct cccagctgtt ccagtgtaac      180
cggaagtcca cattcgatgc agaagtcgat cacctgctgc agctcttctg acggaatgtt      240
ctcaagcacc agctgcgtga tcgttccaaa tgccactttc tctccatggt acatatgatg      300
acattcttcg agtactgtca gaccattgtg aatcgcatgt gctcctgcaa gaccaccact      360
ttcaaagcca attccggaca gcagtgtatt tgcctcgatc actttttcca ctgcttctgt      420
acaggcatct gcttccagtg caagcttcgc cttcacgcct cctccatca gcgtatcaaa       480 acacaatttt gcaagagcca tagctgcccc ggtaatcttt ccgcctgcac aggatgcggc      540
atctgatctc tgacatgctc ttgcttcaaa ataagttgca agagcatctc ccattccggc      600
aacggtaagg cgaaccggtg attctgcaat aatctctgta ccatcatga ccatatccgg       660 attggacggc aggaacaaat actcctcaaa cacaccttct tctgtataaa ttacagaaag      720
tgcgctgcac ggtgcatctg tagatgcgat cgtcggacag atcagaaccg gcgtcttttc      780
ataatatgcc actgcctttg cagtatcaaa atcttacct ccgccgatac cgatcacaac       840
atcacacgct tcttttttca cgatttctcc aagacgtttg atttcttttt tactgcattc      900
accattgaag taatcaaaaa catatccaca ttcttttcct tcaaaacttt tctccaccat      960
tgctccgatt cgcttgtatc ccccttgct gattaggatc agagccttct ttccataatt       1020
ctgagcatat tctcccagtt ttttcatctc tcctgcgccc tgcacatatt ttcccgggct      1080
gatcaatacc tttgccat                                                     1098

<210> SEQ ID NO 9
<211> LENGTH: 1104
<212> TYPE: DNA
<213> ORGANISM: Bacillus coagulans

<400> SEQUENCE: 9
tcatgcccat ttttccttat aataccgccc gacggaatca gcggtaacga ttgctgcgta       60
cacaaggtca ggcgtgactt caaacggcat gttataaatc gtttcgcctt ccgcacagga      120
aagttcagcc acttttcgga gcttttcctc attcagttct ttcacgccca atccccgag       180 cgtgacggga agtccgacac tcaggcagaa ggagaccacc tcttcaattt ccgctttcgg      240
cgcatcttcc aaaatcagct gggcgagggt accgaatgcc acttttttcgc cgtggtacat      300 atgatgggtt tcttcgagca cggtaagccc attatggatc gcatgtgccg cagcaaggcc      360
gccgctttca aaaccgattc cgctcagata cgtattcgct tcaatgattt tttccactgc      420
ttccgtaaca agatgttttt ccgctgccag ttttgctttt aaaccttccg aaatttgcgt      480
gtcataacaa agttttgcaa gcgcgatcgc cgcttccgta acacgcccgc ctgccatcgt      540
cgttttattt gcccgcttag tggcgcgcgc ttcaaaatac gttgcaagcg catctcccat      600 gccgaaacg agcaggcggg caggggcaga ggcaatcact ttcgtatcca taatgacaaa       660
agtcgggttc agcggcagca tcaagtattc ttcaaactcg ccgttctctt tgtaaataac      720
agacagggcg cttgtcgggg catcggtgga agcgatggtc ggcgcgacaa tcaccggaat      780
gttattgtaa tacccgactg cttttgcggt atccaatgtt tttccgccgc cgattccgac      840
aacgacatcg gcttcctcgg atttgctcat ttcacaaagc cgttcgattt ccggtttaga      900
acactcacca ccgaataatg ccatttgata ccccgttttct ttgccggcat agctttcttc      960
aaccgttttg ccgacaaggc cggtgacaaa atcatccgca ataataaatg cttttttgcc      1020 aagccttttcc gtatacgccg aaagcctgga caattcatcg gggccttgta taaacttgct      1080
tggagaggta atgattttcg tcat                                             1104
```

```
<210> SEQ ID NO 10
<211> LENGTH: 1104
<212> TYPE: DNA
<213> ORGANISM: Klebsiella pneumoniae

<400> SEQUENCE: 10
ttattcccat tcctgcagga agcgctgacc atactggtcg gccaccagca gcgcggcgta    60
gacctggtcg gaatcaacgc cgcccggcat attgtgaatg gtttcgcctt cagcgcaggc   120
ggcttccgcc accagacgca ttttggtcgg gatatcacct ttgatatcca gctgcgccag   180
ggtgatcggc agcccaacgc tgtggcacag cgcggcgacg gtctctattt cgtccaccgg   240
cgcattttcc agcaccagct gcgtcagggt tccgaacgcc actttttccc cgtgataata   300
gtgatgggcg tcagggatgg ccgtcatgcc gttatgaatc gcgtgcgccg ccgcgagacc   360
accgctttcg aaacccacgc cgctcagata ggtgttggct tccaccaccc gctccagcgc   420
cggggtgacc acgtgctgtt cggcggccag catcgctttt tcaccctctt cgagtaaggt   480
gttgtagcat agctcggcca ggccagcgc ggcctgggtg cacttcccgc ccgccatggt   540
ggtggcgccc tacgggagc aggcgcgggc ttcgaaccag gtagcagcg catcgccaat   600 cccggcggcc agcaggcggg ccggcgcgcc ggcaacgatc tgcgtatcga caatgaccat   660 gttgggttg cgcggcagca tcaggtagct gtcgaattcc ccttcgtcgg tgtatatcac   720
cgacagcgcg ctgcacggcg catcggtgga ggcgatggtg ggggcgatcg ccaccggcac   780
attcataaag tgggccagcg cttttcgcggt atccagggtt ttgccaccgc cgatccccag   840
cacggcggtg cacttcgcgt tgccggcgat atcgcgtagg cggttgattt cattatgcga   900
acactcaccg ccaaacggcg cgatttcagc cgccaggcca cgtcggcca ggcttttacg   960 cagcatctct tccgcaaacc ccaggacgaa cttatcaccg accaccagcc agcgctcggc  1020
cagcggtttc agatagtcgc cgaggcgctt gatggcgcct gtgccctgga tatattgcc   1080 tggtgattga ataatgcgat ccat                                        1104

<210> SEQ ID NO 11
<211> LENGTH: 1104
<212> TYPE: DNA
<213> ORGANISM: Citrobacter koseri

<400> SEQUENCE: 11
atggaccaca ttattcaatc tcctggtaaa tacatccagg gtgcagatgt catcacacgt    60
cttggagaat atctcaaacc cctggccgaa cgctggctgg tggtcggaga caagtttgtc   120
ttaaattttg cccagtccgc gctggagaaa agtttccagg atgccggact ggctctggaa   180
atcgcgccat ttggcggcga atgttcgcaa aatgaaatcg atcgtctgcg tatcgtcgca   240
gataaagcgc agtgcggcgc cgttctcggc atcggcggcg gcaaaacgct ggataccgcg   300
aaagcgctgg cccactttat ggatgtcccg gtcgctatcg cgccgaccat cgcctctacc   360 gatgcccct gtagcgcgct ttccgtgatc tacaccgatg caggcgagtt tgaacgctat   420
ctgatgctgc gcgtaaccc gaatatggtg attgttgata ccaaaattgt cgcgggcgcg   480
cccgcacgtc tgctggctgc cggtatcggc gatgcgctgg cgacctggtt tgaagcgcgc   540
gcctgttcac gcagcggcgc gaccacgatg gcgggcggca agtgtacaca ggcggcgctc   600 gcgctggcg agttgtgcta taacacgctg atcgaagagg gtgagaaggc catgctggcg   660
gctgagcaga atgtcgtcac gccggcgctg gaacgcgtga ttgaagccaa cacttacctg  720
agcggcgtcg gttttgaaag cggcggtctg gcggcggcgc atgccataca taacggcctg  780
```

```
acggcgattc cagacgcgca tcactactat cacggtgaga aagtggcgtt cggcacgctg      840
acgcaactgg tactggaaaa cgcgccggtt gaagagatcg aaaccgctgc ggcgttgtgc      900
cattccgttg gcctgccgat cacgctggcg caactggata ttaagcagga tattccggcg      960
aagatgcgca cggtggcgga agcctcctgc gcggaaggcg aaaccattca acacatgcct     1020
ggcggcgcca cgccggatca ggtttacgcc gccctgctgg ttgccgacca gtacggtcag     1080
cgtttcctgc aagagtggga ataa                                           1104

<210> SEQ ID NO 12
<211> LENGTH: 1143
<212> TYPE: DNA
<213> ORGANISM: Shigella boydii

<400> SEQUENCE: 12
ttattcccac tcttgcagga aacgctgacc gtactggtcg gctaccagca gagtggcgta      60
aacctgatct ggcgtcgcgc cgccaggcat gttgtggatg gtttcacctt ctgcacatgc     120
cgcttctgcc acaattcgca ttttcgccgg gacatcttct ttaatatcca gttgagcgag     180
agttattggc aaacctaccg catggctaaa tgcagctacg gtttcgattt cctcaaccgg     240
cgcgttttcc agtaccagct gcgtcagcgt accgaatgcc acttttttcac cgtgataata     300 gtgatgcgcg tccgggatag cggtcaggcc gttatgcacc gcatgagccg ccgccagtcc     360
gccgctttca aaaccaacac cgcttaaata ggtgttcgct tcaatcacgc gttccagcgc     420
aggggttact acatgctgtt cggcggcaag catcgctttt tcgccttctt ccagcagagt     480
gttgtagcac agttctgcca gtgccagcgc cgcctgggtg cacttgccgc ccgccatagt     540
ggtagcgccg ctacgggaac aggcgcgtgc ttcaaaccag gttgccagcg catcgccgat     600
acccgccgct aacagacgtg caggagcgcc agcgacgatt ttggtgtcga caatgaccat     660 attcggggtta tttggcaaca gtagatagcg gtcaaactca ccctcatcgg tgtagataac     720
agacaatgcg ctgcacggtg catcggtaga ggcgatagtc ggtgcgatcg ctaccggaac     780
acccatgaaa tgtgccagtg cttttggcagt atcgagggtt tttccgccac cgataccgag     840
aattgcgcca cactgcgcag tctccgcgat gccacgcaga cgatcgatct cattttgcga     900
acattcaccg ccaaacggcg caatttctac taccagtcca gcatctttaa agcttttctc     960
gacagtggat tgagcaaaac ctaaaacaaa tttgtcaccc accactaacc agcgttctgc    1020
cagcggcttc aggtattcgc ccagacgatt aatcacatca gcgccctgga tgtatttacc    1080
cggtgattga ataatgcggt ccataattgc tcctttagag atgagtagtg ccaaatgcgg    1140
cat                                                                  1143

<210> SEQ ID NO 13
<211> LENGTH: 1143
<212> TYPE: DNA
<213> ORGANISM: Klebsiella pneumoniae

<400> SEQUENCE: 13
atgccgcatt tggcactact catctctaaa ggagcaatta tggaccgcat tattcaatca      60
ccgggtaaat acatccaggg cgctgatgtg attaatcgtc tgggcgaata cctgaagccg     120
ctggcagaac gctggttagt ggtgggtgac aaatttgttt taggttttgc tcaatccact     180
gtcgagaaaa gctttaaaga tgctggactg gtagtagaaa ttgcgccgtt ggcggtgaa     240 tgttcgcaaa atgagatcga ccgtctgcgt ggcatcgcgg agactgcgca gtgtggcgca     300
attctcggta tcggtggcgg aaaaaccctc gatactgcca aagcactggc acatttcatg     360
```

-continued

```
ggtgttccgg tagcgatcgc accgactatc gcctctaccg atgcaccgtg cagcgcattg        420
tctgttatct acaccgatga gggtgagttt gaccgctatc tgctgttgcc aaataacccg        480
aatatggtca ttgtcgacac caaaatcgtc gctggcgcac ctgcacgtct gttagcggcg        540
ggtatcggcg atgcgctggc aacctggttt gaagcgcgtg cctgctctcg tagcggcgcg        600
accaccatgg cgggcggcaa gtgcacccag gctgcgctgg cactggctga actgtgctac        660
aacaccctgc tggaagaagg cgaaaaagcg atgcttgctg ccgaacagca tgtagtgact        720
ccggcgctgg agcgcgtgat tgaagcgaac acctatttga gcggtgttgg ttttgaaagt        780
ggtggtctgg ctgcggcgca cgcagtgcat aacggcctga ccgctatccc ggacgcgcat        840
cactattatc acggtgaaaa agtggcattc ggtacgctga cgcagctggt tctggaaaac        900
gcgccggtgg aggaaatcga aaccgtagct gcgcttagcc atgcggtagg tttgccaata        960
actctcgctc aactggatat taagaagat gtcccggcga aaatgcgaat tgtggcagaa       1020
gcggcatgtg cagaaggtga aaccatccac aacatgcctg cgggcgcgac gccagatcag       1080
gtttacgccg ctctgctggt agccgaccag tacggtcagc gtttcctgca agagtgggaa       1140
taa                                                                    1143

<210> SEQ ID NO 14
<211> LENGTH: 1143
<212> TYPE: DNA
<213> ORGANISM: Clostridium butyricum

<400> SEQUENCE: 14
ttatttgcac cctcccttt ttagcttata ctctctgcct atcttatcag ctgcaataat         60
tgatgcagct acatcttcag cgcttattgg gaaaggcata gaatgaatcg attcttcctt        120
aatacatgct tttttagcta cttccataag ttcattttca ttaatactct ccactccaat        180
atctgctaag caaacaggta acccaacttc taaacagaag tctaatactt gatttaattc        240
ttcttttggt gaattttcta atactaattg tgctattgtt ccaaatgcaa cttttttcacc       300 atggaaatat ttatgagttc cttctaatat agtcaatcca tcatgaatag catgtgctcc        360
agctagtcca ccactttcaa atccaatacc tgataaaaga atatttgctt ctataatgtt        420
ttctaatgct ggtgtaacta cattgcagtc tgaagccact tttgcctttg ctccatcatt        480
tataagagtt tcatagcata attttgcaag agctaatgct gtattagttc ctttagcttc        540
attgcaagca cctttctctaa atccacaagg taatcctgca tttacattag aatatgaatt      600
tgaagttgct cttgcttcaa agtatgttga taatgcatct cccattcctg aaaccaagaa        660
acgagttggt gcatttgcaa ttactgtagt gtcaattaaa actacacttg gactttgttt        720
gaaataagca taatcatcaa atgcgccttc atttgtataa agtacagctg aatggcttgt        780
tggtgcatct gtagccgcta ttgttggaac tataattaaa gcttctcctt cagcaacaca        840
tttagcagta tcaatagcct taccaccacc aagaccaatt atgcatgaac atttgttttc        900
actagcaatt tgttgtaatc tacatacctc ttctctagaa cattcaccct taaatccact        960
ttctacaaaa ctaattttaa acttttcaca agttttattt aatttgtcct ttacacgtgt       1020
aacatcatct ttgtgtgcta ttaataaagc tgattctcca aaacttctaa caaagtatcc       1080
caagtttaaa atttcatctt cccttgtac atatttagtt gggcaaataa atgcttttct       1140
cat                                                                    1143

<210> SEQ ID NO 15
<211> LENGTH: 1083
```

<212> TYPE: DNA
<213> ORGANISM: Vibrio sp.

<400> SEQUENCE: 15

| | | | | | |
|---|---|---|---|---|---|
| atggacaaaa | ttattatcag | cccaagcaaa | tacgtccaag | gtgaacaagt | acttacatct | 60 |
| atcgctcact | atgtgaaaac | attgggtgaa | cgtccgttag | tcattgccga | tgagttcgtg | 120 |
| actaacctgg | ttggtgatga | cgtcaaacaa | agctttgctg | acgaaaagct | tccactcact | 180 |
| atgaacattt | ttggtggcga | atgttcgcgc | gttgagatcg | aacgcatcac | ggacatttgt | 240 |
| gcgactcaaa | aacatgatgt | cattgtcggt | attggtggcg | gtaaaacgtt | agatacagca | 300 |
| aaggccgttg | cgttttacac | caaaattcct | gtcgtggtgg | ttcctacaat | tgcctcgact | 360 |
| gatgcgccaa | cctctgctct | tgcggtgata | tacacaccag | aaggtgaatt | tgcggaatac | 420 |
| ttgatgatcc | ctaaaaaccc | agacatggtc | atcatggata | cgtctgtcat | cgcaaaagcc | 480 |
| ccagttcgcc | tactggtatc | ggggatgggc | gatgcgctct | ccacctactt | tgaagctcgt | 540 |
| gccaacatga | cctctggtaa | ggcaacaatg | gccggtggtt | tagcgacacg | ttcagcgcaa | 600 |
| gctcttgcaa | aactttgcta | tgaaaccttg | cttgaagatg | gtgtaaaagc | aaaagctgcg | 660 |
| gtagaaaatg | gtgtgagcac | caaagcggta | gaaaacatta | ttgaagccaa | tacatacctt | 720 |
| agcggtatcg | gttttgaaag | cagtggtcta | gcgggtgctc | acgctattca | taacggccta | 780 |
| accaagctcg | aagagtgtca | tcatctctat | catggtgaga | agtcgcgtt | cggcacactt | 840 |
| gttcaactgg | tgctagaaaa | cgcagcgatg | gaagagatta | tacggttct | cgccttctgc | 900 |
| cgatcggtag | gtctaccaac | caacttgttt | gatatgggcg | ttaaagagct | taatcacgat | 960 |
| aaattgcgcg | aggtcgccga | agcttcaacg | gccgagggag | aaaccatcca | caatatgcca | 1020 |
| ttcccagtga | cggcagaaaa | tgtctactct | gctattctaa | ccgctcatca | actgggccaa | 1080 |
| taa | | | | | | 1083 |

<210> SEQ ID NO 16
<211> LENGTH: 1107
<212> TYPE: DNA
<213> ORGANISM: Serratia proteamaculans

<400> SEQUENCE: 16

| | | | | | |
|---|---|---|---|---|---|
| tcagcttgag | tgttgttgca | gccaggcgtt | gcccagccgg | tctgccgtca | gaatggccgc | 60 |
| ctgtacgctg | gcaggcgtga | cctcgaacgg | catattgtgg | gtggtttcgc | ctgccgcgca | 120 |
| gctggcttcg | gccaccgcca | tgattttctc | cgccgggtcg | ccgctaacgc | ccatctgcgc | 180 |
| cagcgtaatt | ggcaggccga | gacgctgaca | gaaatccagc | accgtttcga | tctgcgccat | 240 |
| gctgctgttt | tgcagcacca | actgtgacag | cgtgccaaac | gccacctttt | cgccgtgata | 300 |
| aaggtgatgg | cactcttcca | gcacggtaaa | accattgtga | atggcatgcg | cggccgccag | 360 |
| gccactgctt | tcgaaaccga | tgccgctcag | ataggtattg | gcctcgataa | tgcgctcgac | 420 |
| cgcctcggtc | accacgccgg | cctcaaccgc | cagcttggcc | ttcacgccct | ctgccagcag | 480 |
| cgtctcatag | cacagccgcg | ccaggctcaa | tgccgccagc | gtggacttgc | cgcccgccat | 540 |
| gctggtcgcc | tgggcatcga | aacaggcctg | tgcttcaaaa | taggttgaaa | gcgcgtcgcc | 600 |
| catgcctgcc | accagcagcc | gcaccggtgc | cttggcgata | atcgagctgt | ccattatcac | 660 |
| catgtccgga | ttactggtgt | ggatcagata | tcgtcaaat | tcgccctgct | cggtgtagat | 720 |
| caccgacagc | gcgctggttg | gcgcatcggt | ggaagcaatg | gtcgggatca | gcaccaccgg | 780 |
| cagatgctgg | taatgggcga | tggccttggc | ggtgtccagc | gttttaccgc | cgccgacgcc | 840 |
| aatcacaccg | cggcagccat | gggccttcag | ttcctggccc | agccggtcga | tttccttatg | 900 |

```
gcagcattcg ccgttgaaca cacaggcgtg atgcttcacc ccgtgctggt gcaggctgcc      960
catcagggta tcgcccgtca gcttcatcac gaagtcgtcg gcgatcacga ataatggtc     1020 ggcaagggct ttcgcatatt cgcccacggc ggccaatgcg ttggcgccct ggatgtactt    1080
gcctggagac tggatgattc tcaacat                                        1107
```

<210> SEQ ID NO 17
<211> LENGTH: 1113
<212> TYPE: DNA
<213> ORGANISM: Geobacillus stearothermophilus

<400> SEQUENCE: 17

```
atggcggcag aaagagtatt tatcagccct gcaaaatatg ttcaaggtaa aaatgtcatt      60
acaaaaatcg cgaattatct tgaaggaatt ggaaacaaga cagtcgtgat agctgatgaa     120
atagtttgga aaatagctgg gcatacaata gtaaacgaat taaaaaaagg aaatattgca     180
gccgaagaag tagttttag cggagaagct tcaagaaacg aggtagaaag aatcgcgaat      240
attgcaagaa aagcagaagc tgctattgta atcggcgttg gtggaggaaa aacgttagat     300
accgcaaaag cggtagcgga tgaattagat gcttatatag tgattgtgcc gacagctgct     360
tcaactgatg cgccaactag tgctctttct gttatatatt ctgatgacgg cgtatttgaa     420
agctaccgtt tttataaaaa gaatccagat cttgtacttg tcgatacgaa aattatcgcc     480
aatgctccgc cacgtttact tgcctctgga atcgctgatg cacttgcaac ttgggtggaa     540
gcacgcagtg ttataaaatc cggaggaaaa acgatggcgg gcggtatccc tacaattgca     600
gctgaagcaa ttgcagaaaa atgtgaacaa actttattca agtacgggaa gcttgcctat     660
gaatcagtaa aagcaaaagt cgtcaccccct gcgttagaag cggtcgtcga agcaaacacg     720
ctccttagcg gactaggttt tgaaagcggc ggtttggcag cggctcatgc tattcataac     780
ggatttaccg cgttagaagg cgaaatacat catttgacac acggagagaa agtggcattt     840
ggtactcttg tccagctcgc tctcgaagaa cattcacaac aagaaattga acgctatatt     900
gagctttatt tgagccttga tttgccagtc acgttggagg acattaaatt aaaagatgct     960
tcacgcgaag atatactaaa agtcgctaaa gcagcaaccg cagaagggga aacaatccat    1020
aatgcattca atgtgacagc tgatgatgta gcagatgcga ttttgctgc tgatcaatat    1080 gcgaaagcat ataagaaaaa acaccgcaaa taa                                1113
```

<210> SEQ ID NO 18
<211> LENGTH: 26
<212> TYPE: DNA
<213> ORGANISM: Artificial Sequence
<220> FEATURE:
<223> OTHER INFORMATION: primer ldhup1F

<400> SEQUENCE: 18

```
ttccatatct gtaagtcccg ctaaag                                           26
```

<210> SEQ ID NO 19
<211> LENGTH: 26
<212> TYPE: DNA
<213> ORGANISM: Artificial Sequence
<220> FEATURE:
<223> OTHER INFORMATION: primer ldhup2R

<400> SEQUENCE: 19

```
attaatacaa tagttttgac aaatcc                                           26
```

```
<210> SEQ ID NO 20
<211> LENGTH: 22
<212> TYPE: DNA
<213> ORGANISM: Artificial Sequence
<220> FEATURE:
<223> OTHER INFORMATION: primer ldhdown3F

<400> SEQUENCE: 20
atataaaaag tcacagtgtg aa                                              22

<210> SEQ ID NO 21
<211> LENGTH: 22
<212> TYPE: DNA
<213> ORGANISM: Artificial Sequence
<220> FEATURE:
<223> OTHER INFORMATION: primer ldhdown4R

<400> SEQUENCE: 21
cacctatttt gcactttttt tc                                              22
```